United States Patent
Molnar et al.

(10) Patent No.: US 8,185,207 B2
(45) Date of Patent: May 22, 2012

(54) MEDICAL DEVICE CONFIGURATION BASED ON SENSED BRAIN SIGNALS

(75) Inventors: Gabriela C. Molnar, Fridley, MN (US); Gregory F. Molnar, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/167,754

(22) Filed: Jun. 24, 2011

(65) Prior Publication Data
US 2011/0251583 A1    Oct. 13, 2011

Related U.S. Application Data

(63) Continuation of application No. 12/133,999, filed on Jun. 5, 2008, now Pat. No. 7,983,757.

(60) Provisional application No. 60/983,016, filed on Oct. 26, 2007.

(51) Int. Cl.
*A61N 1/00* (2006.01)
(52) U.S. Cl. .......................................................... 607/45
(58) Field of Classification Search .................. 600/132, 600/345, 378, 544; 607/2, 42, 45, 46
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 5,702,429 A | 12/1997 | King | |
| 5,814,092 A | 9/1998 | King | |
| 5,913,882 A | 6/1999 | King | |
| 6,018,675 A | 1/2000 | Apkarian et al. | |
| 6,066,163 A | 5/2000 | John | |
| 6,067,467 A | 5/2000 | John | |
| 6,463,328 B1 | 10/2002 | John | |
| 6,907,280 B2 | 6/2005 | Becerra et al. | |
| 7,174,215 B2 | 2/2007 | Bradley | |
| 7,463,927 B1 * | 12/2008 | Chaouat | 607/46 |
| 2002/0042563 A1 | 4/2002 | Becerra et al. | |
| 2003/0100931 A1 * | 5/2003 | Mullett | 607/46 |

(Continued)

FOREIGN PATENT DOCUMENTS
WO    WO 02/38031 A1    5/2002
(Continued)

OTHER PUBLICATIONS

Sarnthein et al., "Increased EEG power and slowed dominant frequency in patients with neurogenic pain," Brain, vol. 129, No. 1, pp. 55-64, Jan. 2006.

(Continued)

*Primary Examiner* — George Manuel
*Assistant Examiner* — Robert Wieland
(74) *Attorney, Agent, or Firm* — Shumaker & Sieffert, P.A.

(57) ABSTRACT

The invention is directed to techniques and systems in which external brain monitoring is used to facilitate implantation and configuration of an implantable medical device. The techniques may create an open loop or closed loop system in which brain signals quantify the efficacy of electrical logical stimulation (or drug therapy via an implantable drug pump) at locations outside of the brain. The techniques may be used to improve placement of leads and electrodes during an implantation procedure, and/or to select or adjust stimulation parameters either during the implantation procedure or possibly following implantation of an implantable medical device. The described techniques have applications for the alleviation of pain, but may find other applications where EEG signals can quantify the efficacy of treatment via an implantable medical device.

53 Claims, 15 Drawing Sheets

U.S. PATENT DOCUMENTS

| | | |
|---|---|---|
| 2004/0096089 A1 | 5/2004 | Borsook et al. |
| 2005/0020905 A1 | 1/2005 | Siddall et al. |
| 2006/0015153 A1 | 1/2006 | Gliner et al. |
| 2006/0089551 A1 | 4/2006 | England |
| 2006/0241374 A1 | 10/2006 | George et al. |
| 2007/0032834 A1 | 2/2007 | Gliner et al. |
| 2007/0179557 A1 | 8/2007 | Maschino et al. |
| 2007/0179558 A1 | 8/2007 | Gliner et al. |
| 2007/0213783 A1 | 9/2007 | Pless |

FOREIGN PATENT DOCUMENTS

| | | |
|---|---|---|
| WO | WO 03/066157 A2 | 8/2003 |
| WO | WO 2006/071891 A1 | 7/2006 |
| WO | WO 2007/111725 A1 | 10/2007 |

OTHER PUBLICATIONS

Apkarian et al., "Human brain mechanisms of pain perception and regulation in health and disease," Eur J Pain 9, pp. 463-484 (2005).
Apkarian et al., "Chronic back pain is associated with decreased prefrontal and thalamic gray matter density," J Neurosci 24, pp. 10410-10415 (2004).
Baliki et al., "Chronic pain and the emotional brain: specific brain activity associated with spontaneous fluctuations of intensity of chronic back pain," J Neurosci 26, pp. 12165-12173 (2006).
Baliki et al., "Beyond feeling: chronic pain hurts the brain, disrupting the default-mode network dynamics," J Neurosci 28, pp. 1398-1403 (2008).
Blair et al., "Dorsal column stimulation. Its effect on the somatosensory evoked response," Arch Neurol 32, pp. 826-829 (1975).
Blamire et al., "Axonal damange in the spinal cord of multiple sclerosis patients detected by magnetic resonance spectroscopy," Magnetic Resonance in Medicine 58, pp. 880-885 (2007).
Borsook et al., "Neuroimaging revolutionizes therapeutic approaches to chronic pain," Mol Pain 3, p. 25 (2007).
Chen et al., Advances in brain imaging of neuropathic pain, Chin Med J (Engl) 121, pp. 653-657 (2008).
Clavo et al., "Cerebral blood flow increase in cancer patients by applying cervical spinal cord stimulation," Neurocirugia (Astur) 18, pp. 28-32 (2007).
El-Khoury et al., "Attenuation of neuropathic pain by segmental and supraspinal activation of the dorsal column system in awake rats," Neuroscience 112, pp. 541-553 (2002).
Grachev et al., "Abnormal brain chemistry in chronic back pain: an in vivo proton magnetic resonance spectroscopy study," Pain 89, pp. 7-18 (2000).
Keshari et al., "Lactic acid and proteoglycans as metabolic markers for discogenic back pain," Spine 33, pp. 312-317 (2008).
Kiriakopoulos et al., "Functional magnetic resonance imaging: a potential tool for the evaluation of spinal cord stimulation: technical case report." Neurosurgery 41, pp. 501-504 (1997).
Marliani et al., "Quantitative proton magnetic resonance spectroscopy of the human cervical spinal cord at 3 Tesla," Magnetic Resonance in Medicine 57, pp. 160-163 (2007).
Meyerson et al., "Mode of action of spinal cord stimulation in neuropathic pain," J Pain Symptom Manage 31, pp. S6-S12 (2006).
Nagamachi et al., "Alteration of regional cerebral blood flow in patients with chronic pain—evaluation before and after epidural spinal cord stimulation," Ann Nucl Med 20, pp. 303-310 (2006).
Oakley et al., "Spinal cord stimulation: mechanisms of action," Spine 27, pp. 2574-2583, (2002).
Peyron et al., "Functional imaging of brain responses to pain. A review and meta-analysis," Neurophysiol Clin 30, pp. 263-288 (2000).
Polacek et al., "Effects of spinal cord stimulation on the cortical somatosensory evoked potentials in failed back surgery syndrome patients," Clin Neurophysiol 118, pp. 1291-1302 (2007).
Rees et al., "Aninociceptive effects of dorsal column stimulations in the rat: involvement of the anterior pretectal nucleus," J Physiol 417, pp. 375-388 (1989).
Schlaier et al., "Effects of spinal cord stimulation on cortical excitability in patients with chronic neuropathic pain: A pilot study," Eur J Pain 11, pp. 863-868 (2007).
Schulman et al, "Thalamocortical dysrhythmia syndrome: MEG imaging of neuropathic pain," Thalamus & Related Systems 3(1), pp. 33-39 (2005).
Siddall et al., "Magnetic resonance spectroscopy detects biochemical changes in the brain associated with chronic low back pain: a preliminary report," Anesth Analg 102, pp. 1164-1168 (2006).
Singer, E. "The Brain in Chronic Pain," Technology Review, Inc., http://www.technologyreview.com, 4 pgs. (2007).
Sindou et al., "Predictive value of somatosensory evoked potentials for long-lasting pain relief after spinal cord stimulation: practical use for patient selection," Neurosurgery 52, pp. 1374-1383 (2003).
Smith, K. "Brain waves reveal intensity of pain," Nature (News) 450, p. 329 (2007).
Sorensen et al., "Differences in metabolites in pain-processing brain regions in patients with diabetes and painful neuropathy," Diabetes Care 31, pp. 980-981 (2008).
Stancak et al., "Functional magnetic resonance imaging of cerebral activation during spinal cord stimulation in failed back surgery syndrome patients," Eur J. Pain, 12 pgs. (2007).
Stephenson et al., "Neuroimaging of Pain: Advances and Future Prospects," J Pain, 13 pgs. (2007).
Theuvenet et al., "Responses to median and tibial nerve stimulation in patients with chronic neuropathic pain," Brain Topogr 11, pp. 305-313 (1999).
"Notification of Transmittal of the International Preliminary Report on Patentability," dated Jan. 25, 2010 for corresponding PCT Application No. PCT/US2008/073424 (11 pgs.).
Reply to Written Opinion dated Mar. 13, 2009 for corresponding PCT Application No. PCT/US2008/073424 (13 pgs.).
"Notification of Transmittal of the International Search Report and the Written Opinion of the International Searching Authority, or the Declaration," dated Nov. 7, 2008 for corresponding PCT Application No. PCT/US2008/073424 (13 pgs.).

* cited by examiner

MEDICAL DEVICE CONFIGURATION BASED ON SENSED BRAIN SIGNALS

This application is a continuation of U.S. patent application Ser. No. 12/133,999 filed on Jun. 5, 2008, which claims the benefit of U.S. Provisional Application No. 60/983,016 filed on Oct. 26, 2007, the entire contents each of which are incorporated herein by reference.

TECHNICAL FIELD

The invention relates to medical device therapy, such as electrical stimulation therapy or drug therapy and, more particularly, to configuration of medical devices.

BACKGROUND

Medical devices, such as implantable medical devices, may be used to deliver electrical stimulation therapy to patients to treat a variety of symptoms or conditions such as chronic pain, tremor, Parkinson's disease, epilepsy, incontinence, or gastroparesis. Electrical stimulation therapy may be applied to deliver stimulation to any of a variety of tissue sites and may comprise neurostimulation, or possibly stimulation of muscle tissue or the like. A medical device may deliver electrical stimulation therapy via a stimulator generator and one or more implantable leads that include electrodes located proximate to the spinal cord, pelvic nerves, or stomach, or within the brain of a patient. The stimulation generator may be external or implantable. For chronic therapy, an implantable stimulation generator is ordinarily desirable. In general, the medical device delivers electrical stimulation therapy in the form of electrical pulses, although continuous waveforms alternatively or additionally may be applied.

Drug pumps, such as implantable drug pumps, are another type of implantable medical device that can be used to treat patients. Drug pumps typically include a reservoir of agents that are delivered to a target site in a controlled manner via one or more implanted catheter. In some cases, electrical stimulation may be used in conjunction with drug therapy.

For electrical stimulation, a clinician, such as a physician or other medical staff, may surgically implant the leads to properly position electrodes at one or more implantation sites desirable for stimulation therapy. The clinician may also select values for a number of programmable parameters in order to define the electrical stimulation therapy to be delivered to a patient. For example, the clinician may select an amplitude, which may be a current or voltage amplitude, and a pulse width for a stimulation waveform to be delivered to the patient, as well as a rate at which the pulses are to be delivered to the patient. The clinician may select, as additional parameters, the particular electrodes within an electrode set to be used to deliver the pulses, and the polarities of the selected electrodes. In some cases, non-pulsed waveforms may be used to drive the stimulation. In any case, a group of parameter values may be referred to as a program in the sense that they drive the electrical stimulation therapy to be delivered to the patient.

For pain treatment, conventional techniques for implantation and configuration of the implantable medical devices may rely on patient feedback. In many cases, however, patient feedback may be an inaccurate or time consuming measure of the accuracy of the electrode placement and/or the configuration of the stimulation parameters of an implantable electrical stimulation device.

SUMMARY

In general, the invention is directed to techniques and systems in which brain signal sensing is used to facilitate configuration of a medical device that is used to deliver therapy to a target site outside the brain. Sensing of one or more brain signals may provide an indication of the efficacy of an electrical stimulation therapy, and may be particularly effective for stimulation therapy for the treatment of pain. Configuration of the medical device may include implantation, programming and/or operational control of the medical device based on one or more sensed brain signals, parameters and/or characteristics. The medical device may be external or implantable, or combine both external and implantable components. Brain signal sensing may be obtained by one or more external sensing devices, implantable sensing devices, or combinations of external and implantable sensing devices.

The techniques may support an open loop system, or a closed loop system in which sensed brain signals are used to quantify the efficacy of therapy, such as electrical stimulation therapy. The techniques may be used to improve placement of leads and electrodes during an implantation procedure, and/or to select or adjust stimulation parameters for device programming either during the implantation procedure or possibly following implantation of an implantable medical device. Additionally, or alternatively, the techniques may be used to control one or more stimulation parameters based on one or more sensed brain signals during operation of the medical device. Although the techniques are primarily described as being applicable to electrical stimulation therapy, similar techniques may also be used to configure or adjust the delivery of drug therapy via an implanted drug pump. The described techniques have applications for the alleviation of pain, but may find other applications where brain signals can be used to indicate and possibly quantify the efficacy of treatment via an implanted medical device.

In one embodiment, the invention provides a method comprising monitoring brain signals of a brain via an external brain activity monitoring device, and adjusting electrical stimulation delivered via one or more implanted electrodes to one or more locations outside of the brain based on the brain signals.

In another embodiment, the invention provides a method comprising monitoring brain signals via an external brain activity monitoring device, and adjusting drug delivery to one or more locations outside of the brain based on the brain signals.

In another embodiment, the invention provides a system comprising an external brain activity monitoring device that monitors brain signals of a brain of a patient, one or more implantable electrodes that deliver electrical stimulation to one or more locations within the patient outside of the brain, and a stimulator device that generates the electrical stimulation delivered by the one or more implantable electrodes, wherein the stimulator device adjusts the electrical stimulation based on the brain signals. Alternatively, the external brain activity monitoring device could also be connected to a programmer that controls the output of the stimulator device and delivers stimulation to one or more locations through one or more implanted electrodes.

In another embodiment, the invention provides a system comprising an external brain activity monitoring device that monitors brain signals of a brain of a patient, and an implantable drug pump that delivers drugs to a location outside of the brain, and adjusts drug delivery based on the brain signals.

In another embodiment, the invention provides a method comprising monitoring brain signals of a brain, and adjusting electrical stimulation delivered via one or more implanted electrodes based on the brain signals to alleviate pain to a patient.

In another embodiment, the invention provides a system comprising means for monitoring brain signals of a brain via an external brain activity monitoring device, and means for adjusting electrical stimulation delivered via one or more implantable electrodes to one or more locations outside of the brain based on the brain signals.

In another embodiment, the invention provides a system comprising means for monitoring brain signals via an external brain activity monitoring device, and means for adjusting drug delivery to one or more locations outside of the brain based on the brain signals.

In another embodiment, a method comprises monitoring brain signals of a brain via an external brain activity monitoring device, adjusting therapy delivered to one or more locations outside of the brain based on the brain signals, and selecting a patient for treatment via an implantable medical device based on brain response to the therapy.

The invention may provide a number of advantages. For example, the invention may improve implantation of electrodes disposed on medical leads relative to precise target sites, which may be desirable for the delivery of electrical stimulation therapy. In a similar way, the invention may improve implantation of catheters relative to precise target sites for implanted drug pumps. In addition, the invention may allow for configuration and reconfiguration of implanted medical devices, e.g., following the implantation procedure. In this case, movement of electrodes, leads or catheters, following the implantation procedure may be addressed by monitoring brain signals and adjusting the operation of the device based on the brain signals. Operational adjustments to stimulation parameters or other operational parameters of a medical device may also be supported, e.g., following the implantation procedure.

In some cases, the invention may be fully automated, e.g., for the selection of stimulation parameters, thereby reducing the possibility of human error. Such automation may be useful during the implantation procedure to configure the device, or following the implantation procedure to re-configure the device. By using brain signals to quantify the brain response to electrical stimulation or drug delivery, the efficacy of treatment may be improved.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
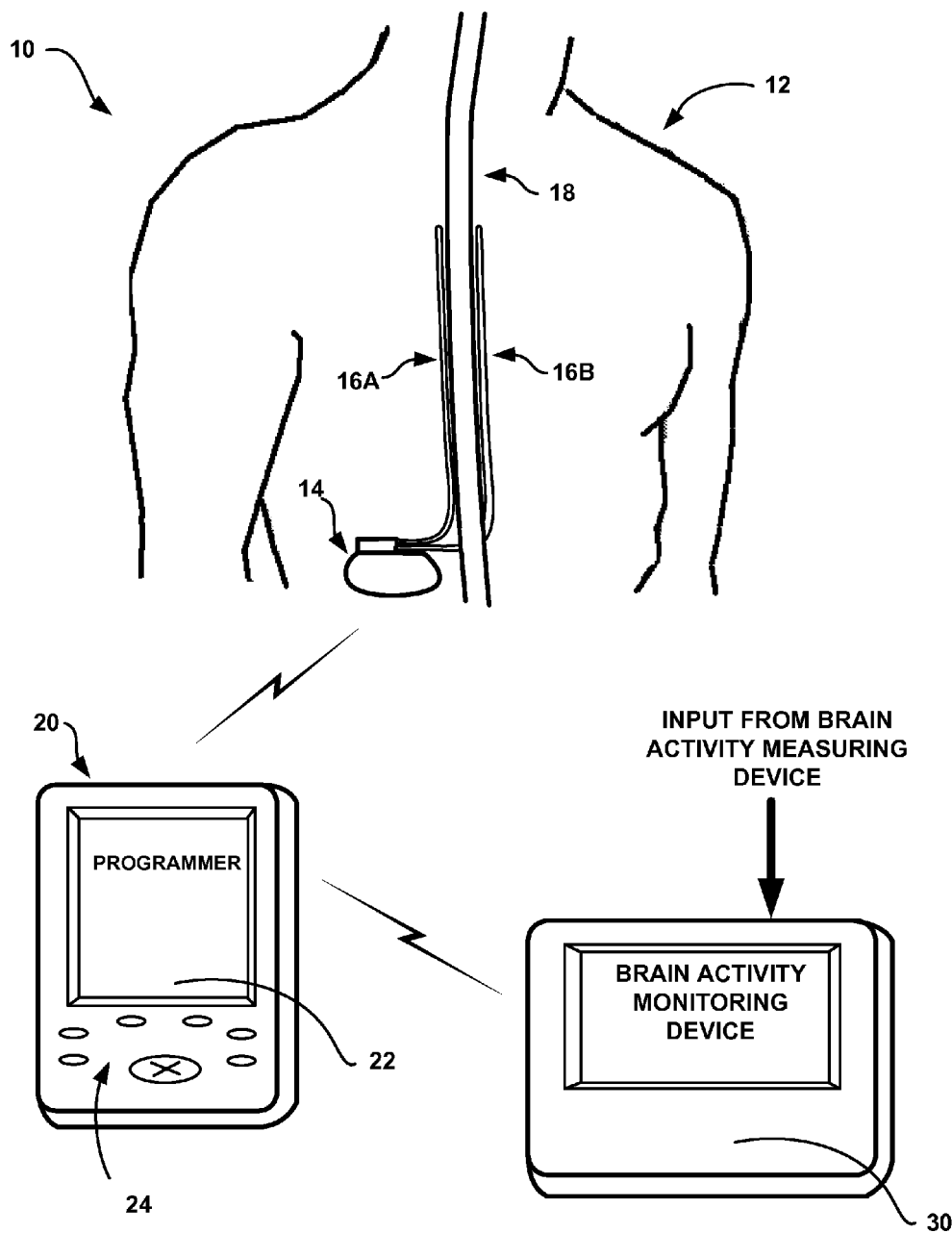
FIG. 1 is a diagram illustrating an example system for programming and delivering electrical stimulation therapy to a stimulation site outside the brain based on detected brain signals.

The invention is directed to techniques and systems in which external brain monitoring, such as monitoring of electroencephalogram (EEG) signals or magnetoencelphalogram (MEG) signals, is used to facilitate implantation and/or configuration of an implantable medical device. The brain is comprised of several structures including the cerebral hemispheres, the brainstem, and the cerebellum. The techniques may support a closed loop system in which measured brain response indicates and possibly quantifies the efficacy of electrical logical stimulation, e.g., at locations outside of the brain. As an example, the techniques may be used for configuration of a medical device for spinal cord stimulation (SCS). In this case, brain signals may indicate efficacy of SCS in alleviating pain. The techniques may be used to improve placement of leads and electrodes during an implantation procedure, and/or to select or adjust stimulation parameters either during the implantation procedure or possibly following implantation of a medical device. Hence, the techniques may be used to support implantation, programming and/or operational control of the medical device.

The techniques are primarily described as being applicable to electrical stimulation therapy such as neurostimulation. However, similar techniques may also be used to adjust the delivery of drug therapy via an implanted drug pump, or possibly adjust electrical stimulation to other types of tissue such as muscle tissue. The techniques have applications for the alleviation of pain, e.g., via spinal cord stimulation (SCS), occipital nerve stimulation, peripheral nerve field stimulation (PFNS), pelvic nerve stimulation, gastric stimulation, or the like, but may find other applications where detected signals of the brain can quantify the efficacy of treatment delivered by an implanted medical device to locations outside the brain.

There are various brain centers involved in the processing of pain. When a patient feels pain, different areas of the cortex may become activated, including primary and secondary somatosensory cortices, thalamus, cingulate and insular cortices. Different brain areas are associated with different components of pain, including sensory (primary somatosensory cortex, sensory thalamus), affective (cingulate, prefrontal, and insular cortices as well as secondary somatosensory cortex, thalamus), cognitive and psychological (cingulate cortex). The patterns of brain stimulation are different between spontaneous chronic pain and acute pain. Painful stimuli may induce oscillations in the brain in specific frequency ranges, such as a frequency range of 40-100 Hz, and amplitudes of these oscillations may be related to the subjective experience of pain. Spinal cord stimulation may also induce neuronal oscillations in the mesial frontal cortex involving the supplementary motor area and primary somatosensory cortex, around the frequency of the stimulation. The invention may involve a method in which an objective biomarker (e.g., an external measurement or quantification of a brain signal) is used to sense and analyze cortical oscillations to create a closed-loop spinal cord stimulation (SCS) therapy for purposes of patient selection (e.g., selecting responders vs. non-responders for therapy), guiding lead placement or programming the implantable medical device. The signals or biomarkers may relate to one or more components of pain, whether it is sensory, affective, cognitive or psychological, the state itself, or the evoked effects of SCS at the level of the brain. Various metrics may be defined based on sensed brain signals to determine, quantify or measure the effectiveness of the therapy.

FIG. 1 is a diagram illustrating an example system 10 for programming electrical stimulation therapy for and delivering electrical stimulation therapy to a patient 12. System 10 includes an implantable medical device (IMD) 14 that is implanted in patient 12 to deliver electrical stimulation therapy to patient 12. IMD 14 may be an implantable pulse generator (IPG) or other type of stimulator device, and may deliver electrical stimulation therapy to patient 12 in the form of electrical pulses. As discussed below, however, the invention may also have application with an external stimulation generator with leads coupled via a percutaneous lead extension, e.g., particularly during an implantation procedure for medical leads.

In the example of FIG. 1, IMD 14 delivers electrical stimulation therapy to patient 12 via implantable leads 16A and 16B (collectively "leads 16"). Leads 16 may, as shown in FIG. 1, be implanted proximate to the spinal cord 18 of patient 12, and IMD 14 may deliver SCS therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to other locations for alleviation of pain or other therapeutic purposes.

IMD 14 delivers electrical stimulation therapy to patient 12 according to one or more electrical stimulation therapy programs. An electrical stimulation therapy program may include values for a number of parameters, and the parameter values define the electrical stimulation therapy delivered according to that program. In embodiments where IMD 14 delivers electrical stimulation therapy in the form of electrical pulses, the parameters may include pulse voltage or current amplitudes, pulse widths, pulse rates, pulse waveform shapes (e.g., mimicking more physiological activity), pulse duty cycles, two or more frequencies, pulse widths or amplitudes delivered regularly or randomly, and the like. Further, each of leads 16 includes electrodes (not shown in FIG. 1), and the parameters for a program may include information identifying which electrodes have been selected for delivery of pulses according to the program, i.e., an electrode combination, and the polarities of the selected electrodes in the electrode combination.

As mentioned above, a selected subset of the electrodes located on leads 16 and the polarities of the electrodes of the subset collectively define an "electrode combination." Electrode combinations refer to combinations of single or multiple cathode electrodes and single or multiple anode electrodes. Stimulation current flows between the cathodes and anodes for delivery of electrical stimulation therapy.

System 10 also includes a programmer 20. Programmer 20 may, as shown in FIG. 1, be a handheld computing device. Programmer 20 may include a display 22, such as a LCD or LED display, to display information to a user (such as the patient, or the patient's physician or clinician). Programmer 20 may also include a keypad 24, which may be used by a user to interact with programmer 20. In some embodiments, display 22 may be a touch screen display, and a user may interact with programmer 20 via display 22. A user may also interact with programmer 20 using peripheral pointing devices, such as a stylus or mouse. Keypad 24 may take the form of an alphanumeric keypad or a reduced set of keys associated with particular functions. A wide variety of other programmer configurations may be used in accordance with the invention.

A clinician (not shown) may use programmer 20 to program electrical stimulation therapy for patient 12. In particular, the clinician may use programmer 20 to create electrical stimulation therapy programs. As part of the program creation process, programmer 20 may allow the clinician to identify electrode combinations that enable IMD 14 to deliver electrical stimulation therapy that is desirable in terms of, for example, symptom relief, coverage area relative to symptom area, and side effects. Programmer 20 may also allow the clinician to identify electrode combinations that enable IMD 14 to deliver effective electrical stimulation therapy with desirable device performance characteristics, e.g., low battery consumption. In other examples, programmer 20 may comprise a patient programmer.

In addition, in some cases, programmer 20 may select or adjust parameters associated with the stimulation therapy to be delivered by IMD 14 in an automated fashion, possibly allowing patient 12 to re-configure IMD 14 via programmer 20. In particular, as described in detail below, system 10 may form a closed loop automated system in which brain activity of patient 12 is monitored in response to therapy by IMD 14, and the monitored brain activity facilitates adjustments to the therapy delivered by IMD 14 via programming adjustments sent from programmer 20.

In particular, system 10 may further include a brain activity monitoring device 30. Brain activity monitoring device 30 receives input from a brain activity measuring device (not shown in FIG. 1). The brain activity measuring device, for example, may comprise an EEG or MEG device that is placed over or attached to the head of patient 12. The brain activity measuring device may include external electrodes that couple to the skull of patient 12, or in some cases, screws may be attached to the skull of patient 12 to improve electromagnetic coupling and brain signal detection by the brain activity measuring device. Most basically, however, the brain activity measuring device may comprise two or more electrodes or sensors that record brain signals at two or more different sites on the scalp or head of patient 12, and the brain activity measuring device is not necessarily limited to any size, shape or configuration.

Again, system 10 may form a closed loop automated system in which brain signals of patient 12 are monitored in response to therapy by IMD 14, and the monitored brain signals facilitate adjustments to the therapy delivered by IMD 14 via programming adjustments sent from programmer 20. However, system 10 is only exemplary, as many other closed loops systems could be used in which external and internal devices form the loop. Importantly, brain signals responsive to therapy delivered outside of the brain by an implanted medical device are used to configure and/or adjust such therapy.

In other examples, one or more of the components of system 10 could be combined. As an example, the brain activity measuring device (not illustrated in FIG. 1) and brain activity monitoring device 30 could be combined into a brain activity measuring and monitoring device worn on the head of patient 12. In this case, the patient could use the brain activity measuring and monitoring device to cause the programmer to re-calibrate stimulation parameters, possibly without the aid of a clinician.

Also, other closed loop system configurations could be employed for a trial stage of treatment or during the implantation procedure. For example, during the implantation procedure, IMD 14 may be an external stimulator, which is connected to percutaneously implanted leads 16A and 16B. Percutaneous lead extensions may also be used in this case. In any case, the brain activity response to stimulation may be used not only to adjust or select stimulation parameters, but may aid a physician in achieving proper placement of leads 16A and 16B. For example, the physician may view and interpret the brain response shown in brain activity monitoring device 30 upon application of stimulation energy via leads 16A and/or 16B to determine whether leads 16A and/or 16B, or particular electrodes carried by such leads, are implanted in the correct location for effective therapy. An external stimulator used during the implantation procedure may combine the functionality of IMD 14 and programmer 20 into an external device that both generates the electrical stimulation delivered by leads 16A and 16B, and searches and adjusts for desirable electrode combinations and desirable stimulation parameters.

In some cases, programmer 20 may control IMD 14 to test electrode combinations in order to allow a clinician to identify desirable combinations in an efficient manner. Furthermore, the selection of desirable electrode combinations may be automated based on the brain activity response to different combinations. Programmer 20 may select electrode combinations based on an electrode combination search algorithm, and based on the best brain activity response, may select that combination that yields the best therapeutic result. In particular, according to such an algorithm, programmer 20 may first control IMD 14 to test one or more electrodes to identify the electrode which will act as a first cathode electrode, and then control IMD 14 to test combinations that include the first cathode in an order that is based on the proximity of other electrodes in the combination to the first cathode.

By controlling IMD 14 to test electrode combinations in such an order, programmer 20 may quickly identify desirable electrode combinations. Regardless of whether the process is fully automated, or used in conjunction with a clinician that decides which electrode combination and stimulation parameters to use, the process uses brain monitoring to guide such decisions for the type of stimulation, lead placement, and electrode combinations to be used. The brain monitoring may be achieved by an external or implanted brain sensing device. The stimulation may be performed outside of the brain, e.g., along the spine or some other anatomical structure outside the brain, but the brain response guides the clinician (or programmer 20 for automated embodiments) to make decisions about the therapy, e.g., for configuration of a stimulation device. Accordingly, the neurological physiology of patient 12 (i.e., the connections between the brain of patient 12 and the nerves outside of the brain) forms part of the loop.

Programmer 20 may communicate with IMD 14 via telemetry techniques known in the art. For example, programmer 20 may communicate with IMD 14 via an RF telemetry head (not shown). Information identifying desirable combinations of electrodes identified by the clinician may be stored as part of electrical stimulation therapy programs. Electrical stimulation therapy programs created by the clinician using programmer 20 may be transmitted to IMD 14 via telemetry, and/or may be transmitted to another programmer (not shown), e.g., a patient programmer, that is used by patient 12 to control the delivery of electrical stimulation therapy by IMD 14. Stimulation parameters selected based on brain response may be communicated from programmer 20 to IMD 14 via telemetry. Also, sensed parameters may be telemetrically communicated to programmer 20 from a sensor external to the brain (or possibly from one or more sensors implanted on or in the brain).

Figure 2:
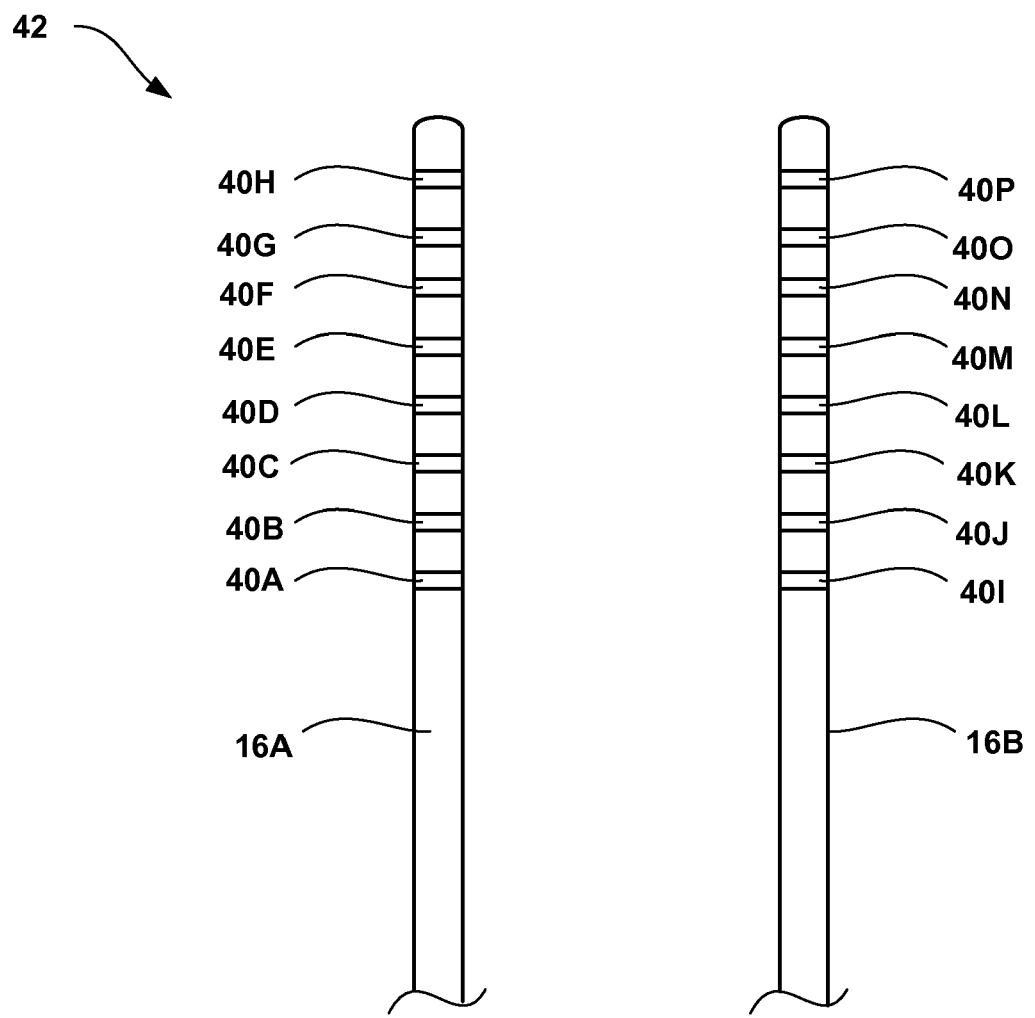
FIG. 2 is a diagram illustrating an example electrode set that may be implanted within the patient.

FIG. 2 is a block diagram illustrating an example configuration of leads 16. In the example configuration, lead 16A includes electrodes 40A-H, and lead 16B includes electrodes 40I-P. Electrodes 40A-P (collectively "electrodes 40") may be ring electrodes.

Electrodes 40 collectively form an electrode set 42 implanted within patient 12. As shown in FIG. 2, electrode set 42 includes eight electrodes on each of the two leads 16, which, as shown in FIG. 1, are implanted such that they are substantially parallel to each other and spinal cord 18, on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrode set 42 may be described as a two-by-eight, side-by-side, upwardly oriented configuration.

Such a configuration is commonly used to provide SCS therapy. However, programmer 20 may be used to identify desirable combinations of electrodes within electrode sets that are configured in any way, and used to provide any type electrical stimulation therapy. For example, a single lead including four or eight electrodes, two leads including four electrodes per lead, in-line leads, and offset leads, all of which may be oriented in any manner relative to patient 12, provide electrode set configurations that may be searched by programmer 20. In another example, the leads may comprise paddle-shaped leads that have two or more electrodes. The invention is not limited to any particular lead size, shape or configuration, and could even be implemented using implanted electrodes that are not disposed on leads.

IMD 14 (FIG. 1) may deliver electrical stimulation via any combination of electrodes 40. IMD 14 may independently activate each electrode 40 of set 42 to act as a cathode or anode for a combination, and each combination will include at least one cathode and at least one anode. In some embodiments, a combination may include a single electrode 40 acting as the cathode, with a can of IMD 14, i.e., the IMD housing, acting as the anode for the combination.

In an electrode combination, electrons flow from the one or more electrodes acting as anodes for the combination to the one or more electrodes acting as cathodes for the combination. The current between anodes and cathodes may stimulate neurons between and proximate to the anodes and cathodes. Generally speaking, an electrode combination enables desirable electrical stimulation therapy when current is delivered in a direction and with an intensity sufficient to stimulate specific neurons or a sufficient number of specific neurons to alleviate a symptom without causing unacceptable side effects. Further, an electrode combination enables desirable electrical stimulation therapy when the symptom is alleviated without resorting to undesirably high pulse amplitudes.

As mentioned above, programmer 20 may identify and/or select individual electrodes 40 or electrode combinations based on brain activity response to such stimulation. For example, measured brain signals may indicate whether the stimulation is efficacious in relieving pain, as may possibly be used to determine a level of pain relief. Programmer 20 may select an appropriate search algorithm based on the configuration of electrode set 42, and may select electrodes 40 or electrode combinations based on brain activity response to different combinations. Programmer 20 controls IMD 14 to test a selected electrode 40 or electrode combination by controlling IMD 14 to deliver electrical stimulation via the selected electrode 40 or combination.

Programmer 20 may first control IMD 14 to test one or more of electrodes 40 individually to identify the individual electrode or electrodes 40 which will act as a first cathode. Generally, a clinician implants leads 16 in a location such that the center of electrode set 42 is proximate to an area that the clinician believes should be stimulated in order to alleviate symptoms. Therefore, programmer 20 may test electrodes 40 as the first cathode in an order such that electrodes 40 located centrally within electrode set 42, e.g., electrodes 40D-E and 40L-M illustrated in FIG. 2, are tested before peripherally located electrodes. If the clinician's estimation of the target region is inaccurate, programmer 20 may continue to test individual electrodes 40 in such an order until one of the electrodes 40 that enables desirable electrical stimulation therapy when activated as the first cathode is identified, e.g., based on the patients brain response to the electrical stimulation.

Programmer 20 may then control IMD 14 to test electrode combinations that include the first cathode. Programmer 20 may control IMD 14 to try different ones of electrodes 40 as the first anode in a pair with the first cathode, and may add additional anodes and/or cathodes. Programmer 20 may control IMD 14 to test remaining electrodes 40 as first anodes, and additional anodes or cathodes, in an order that is based on the proximity of the remaining electrodes 40 to the electrode 40 acting as the first cathode for the electrode combination. The order may be based on decreasing proximity of the remaining electrodes 40 to the electrode acting as the first cathode, e.g., electrodes will be tested in order of increasing distance from the first cathode.

Generally, electrode combinations that include cathodes and anodes in closer proximity may be more likely to enable desirable electrical stimulation therapy. Regardless, however, the appropriate response can be quantified externally by the brain response of the patient. Therefore, by testing electrode combinations and quantifying the efficacy of such combinations based on brain response, the desirable combination (which may also depend on a particular set of amplitude, pulse width and pulse rate parameters) can be programmed into the IMD. Furthermore, this process may be performed post-implantation, to adjust electrode combinations and account for possible movement or dislodgment of leads 16A and 16B within the patient. The response of the patient's brain facilitates such determinations. In particular, the combinations of electrodes and/or parameters that yield better efficacy during testing, as indicated by the brain signals, may be selected for delivery of stimulation on an ongoing, chronic basis.

Figure 3:
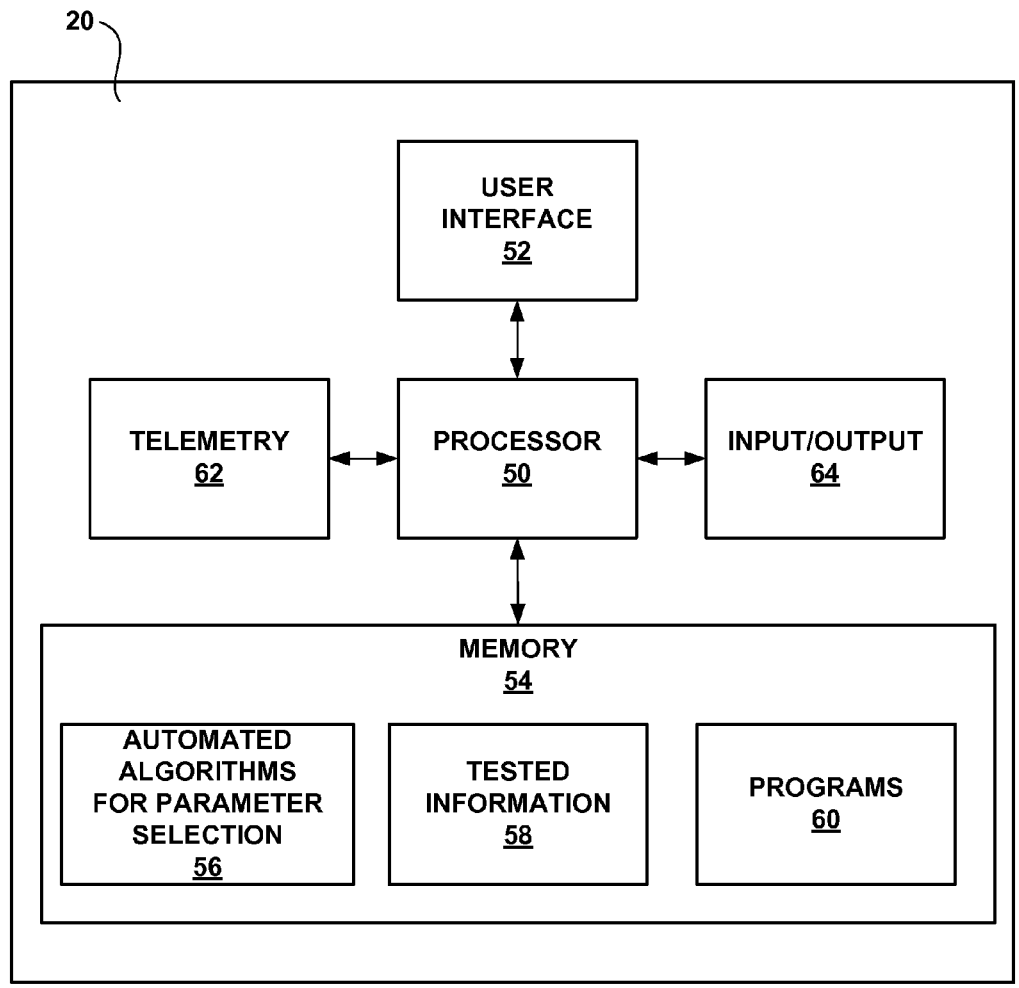
FIG. 3 is a block diagram illustrating an example programming device that may receive signals from a brain sensing device or an external brain monitoring device, and program an implantable medical device based on the received signals.

FIG. 3 is a block diagram illustrating an example configuration of programmer 20. A clinician may interact with a processor 50 via a user interface 52 in order to select electrode combinations, and stimulation parameters as described herein. The clinician may use the patient's brain response to aid such decisions. Alternatively, programmer 20 may select electrode combinations and stimulation parameters in an automated fashion based on the patient's brain response to different electrode combinations and stimulation parameters.

User interface 52 may include display 22 and keypad 24, and may also include a touch screen or peripheral pointing devices as described above. Processor 50 may also provide a graphical user interface (GUI) via user interface 52 to facilitate interaction with a clinician. Processor 50 may include one or more microprocessors, controllers, DSPs, ASICs, FPGAs, discrete logic circuitry, or the like.

Programmer 20 also includes a memory 54. Memory 54 may include program instructions that, when executed by processor 50, cause programmer 20 to perform one or more of the functions described herein. For example, processor may execute a selected one of automated algorithms 56 stored within memory 54 to automate stimulation parameter selection. Algorithms may also be used to automate electrode combination selections.

Processor 50 may collect information relating to tested electrode combinations and stimulation parameters, and store the tested information 58 in memory 54 for later retrieval and review by the clinician to facilitate identification of desirable electrode combinations. In some cases, tested information 58 may be stored and used to make automated decisions regarding the desirable electrode combinations and electrical stimulation parameters.

Pre-developed electrical stimulation therapy programs 60 may be stored in memory 54, for testing and possible use if such programs achieve the desired brain response. Memory 54 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Spinal cord stimulation is currently approved for the treatment of chronic, intractable pain of the trunk and/or limbs including unilateral or bilateral pain associated with Failed Back Syndrome (FBS) and Complex Regional Pain Syndrome (CRPS). Current methods for patient programming involve extensive trial-and-error methods in order to select the stimulation parameters for each individual patient. In this case, subjective patient feedback is required in order to determine a desirable electrode configuration and parameters of stimulation.

Biomarkers exist that can provide an indication of a disease state for persons suffering from certain neurological disorders. There is evidence that in neuropathic pain patients, brain activity changes relative to the brain activity of healthy patients that do not experience neuropathic pain. SCS itself may also evoke certain patterns of brain signals that reflect the efficacy of the site of stimulation in the spinal cord. This disclosure, in some aspects, provides a system that delivers electrical stimulation or drug therapy to treat patients, and the system concurrently measures neurological biomarkers as an indication of therapy effectiveness. For example, EEG signals may be monitored to determine whether therapy is effective in reducing or eliminating symptoms such as pain. One or more characteristics of the EEG signals, such as amplitude, frequency, power, or ratios of such characteristics in different frequency bands may be effective in indicating whether therapy is effective in relieving symptoms. Metrics may be generated to measure or quantify one or more of these characteristics.

As an illustration, there is evidence that in central neuropathic pain patients, higher spectral power is exhibited over the 2-25 Hz frequency with the dominant peak shifting to lower frequencies in such patients relative to control patients. In the presence of neuropathic pain, overactivation (e.g., an undesirable increase in brain signals) is observed in the theta (e.g., 4-9 Hz) and beta (e.g., 12-30 Hz) frequency bands and may be localized to areas associated with the cortical pain matrix. In particular, in the presence of neuropathic pain, overactivation in the low beta range has been observed in midprefrontal areas of a patient's brain, while insular and rostral anterior cingulate cortices overactivation have been observed in both theta and beta frequency ranges. The power and frequency can be analyzed within several frequency bands (up to 300 Hz) in a painful and nonpainful state for a given patient. Changes from an expected baseline may lead to an adaptive therapy that is titrated when a certain threshold is reached. For example, stimulation parameters such as amplitude, pulse width and/or pulse rate, and waveform may be adjusted based on information sensed from the brain to improve therapeutic efficacy.

Further, changes in gamma oscillations (e.g., 40-100 Hz) may be linked to the subjective experience of pain. The magnitude of these oscillations may be detected at the cortical level and perhaps used to further titrate therapy. It may be possible to obtain a biomarker based on EEG frequency bands that could be a marker for therapy efficacy. This biomarker may be used for patient selection, i.e., selection of a patient as a candidate for SCS or some other applicable pain therapy, stimulus parameter selection/programming, and a therapy biomarker for monitoring or closed-loop feedback control for stimulation parameters, such as SCS parameters.

Evoked responses in the brain due to SCS may arise at similar frequencies. The special location, phase and onset time of these brain responses could indicate the optimal therapeutic site in the spinal cord.

In some embodiments, the invention contemplates the use of an external modality, such as external electrodes placed on the head, neck, face, and/or scalp, to measure abnormalities in the electromagnetic signals of the brain (i.e. EEG, MEG). Such abnormalities may be used to select appropriate Subcutaneous Stimulation (SQS), spinal cord simulation (SCS), Peripheral Nerve Stimulation (PNS) including Occipital Nerve Stimulation (ONS), Motor Cortex Stimulation (MCS) or pump titration for neuropathic/neurogenic pain or headache patients. In the context of this disclosure, titration may generally refer to adjustment of one or more applicable therapeutic parameters, dosages, or the like.

The invention, in some embodiments, may involve measurement of a cortical biomarker for pain therapy objectification. There may be a dominance of high power, low frequency activity in the theta and beta bands in central neuropathic pain patients (thalamocortical dysrhythmia). The invention may determine an EEG power spectrum threshold for a patient, and activate therapy (i.e. closed-loop embodiment) if the sensed EEG power spectrum falls below this threshold (e.g., a combination of frequency and power, or frequency only).

In particular, in some embodiments, the invention may involve detecting a cortical, physiological biomarker that could be used as objectification of a therapeutic response. In addition, the invention may involve titration, programming, and/or optimization of SCS therapy, and proposes applications related to closed loop therapies for SCS during trial, during implantation, and following implantation of an implantable medical device.

The invention may also identify a recruiting rhythm to identify patients who will have good outcomes with SCS, and selection of SCS parameters for such patients. This may involve detecting the stimulation frequency (or harmonic or subharmonic) at the level of the cortex, such as at the somatosensory cortex.

The invention may involve the use of biomarkers for the following applications:
1. A system for patient selection (i.e., identification of a candidate for effective SCS therapy) based on brain response for SCS during trial. For example, if an EEG signal biomarker, e.g., in one or more selected frequency ranges, is greater than or less than an applicable threshold value, the patient may present as a candidate for SCS, or another applicable pain therapy.
2. A system for stimulus parameter selection and adjustment using automated programming algorithms based on brain response without the need for excessive patient feedback during trial, implant and after implant. For example, an automated system may adjust applicable therapy parameters based on sensed EEG biomarker signals, e.g., in one or more selected frequency ranges.
3. A system for guiding lead/catheter placement based on brain response in the operating room during implant (relevant changes in biomarker indicate optimal position and stimulation parameters).

In addition, other potential applications may include:
1. A system for detection of lead/catheter migration based on brain response that will create an alert to the patient. For example, if a biomarker signal changes relative to threshold or reference value, the change may be indicative of undesirable migration relative to a target therapy site. The change would trigger an audible, visual, or vibratory alert from the implanted device, patient programmer, or other external device. This may signal the patient to visit their physician, or alternatively the alert may trigger automated programming algorithms (e.g., try and find a correct set of anodes of cathodes and stimulus parameters) to try and recapture therapy.
2. A method using a particular therapy biomarker to distinguish between placebo effects and SCS therapeutic effects.
3. Titration of therapy according to pain intensity level of patient (gamma oscillation power levels may correlate with subjective perception of pain intensity)

The invention may measure a cortical biomarker for pain for therapy objectification. Some studies have shown a dominance of high power, low frequency activity in the theta and beta bands in neuropathic pain patients. The invention may determine a threshold for a patient and activate therapy if one or more measures of brain signals (e.g., power, frequency, or a combination of power levels at different frequency bands) falls below this the threshold.
4. A robust and accurate biomarker could be used to distinguish between placebo effects and SCS therapeutic effects.

The invention, in an example embodiment, may measure a cortical biomarker for subjective pain intensity. Gamma band power may correlate with pain intensity of a healthy patient. Also, the intensity of spontaneous pain varies with time. The invention may titrate therapy, such as electrical stimulation parameters or drug dosages, rates, or durations, depending on pain level and pain intensity.

The invention, in some embodiments, may identify rhythms, such as recruitment rhythms, harmonic or subharmonics of stimulation frequency, at the level of the cortex (i.e. determine whether stimulation detected at the cortical level).

In accordance with the invention, sensing locations used to quantify the efficacy of stimulation treatment may include locations at or in external proximity to the cerebral cortex, or possibly locations in the spinal cord or peripheral nervous system. Other locations may include locations at or in external proximity to the somatosensory cortex (SI, SII), the anterior cingulate cortex, the prefrontal cortex, and/or the insular cortex. External or implanted electrodes may be positioned to obtain sensed signals from such locations. Alternatively, signal processing and analysis could be performed including source localization techniques (such as the so-called "LORETA" techniques) to confirm that the electrical activity recorded at the scalp is originating approximately from deeper areas of the brain known to be associated with the sensory and affective components of pain (such as in the cingulate cortex, the thalamus, and/or other locations known to be associated with pain).

Figure 4:
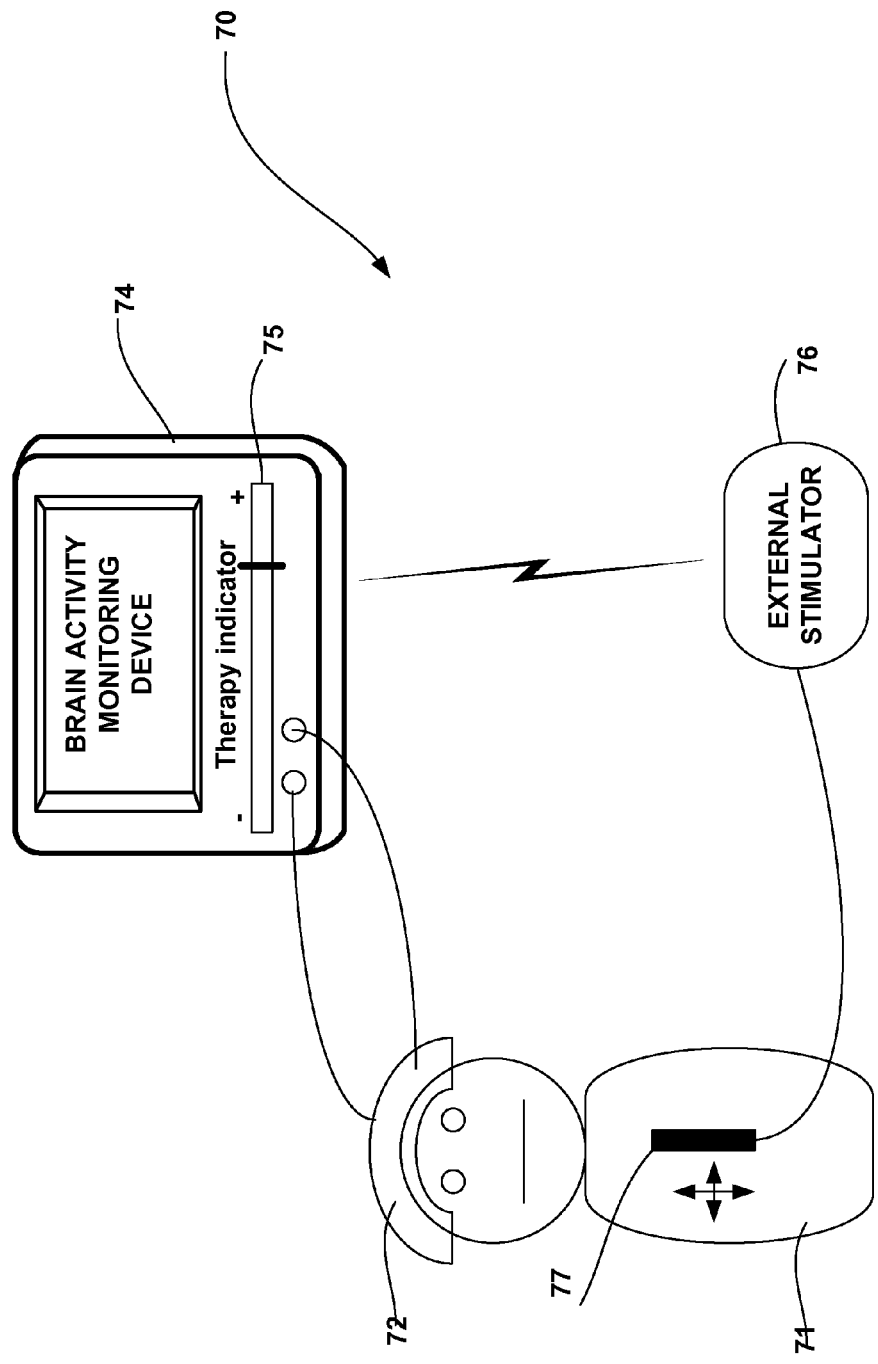
FIG. 4 is a diagram illustrating a closed-loop feedback system according to the invention during an implantation procedure.

FIG. 4 is a diagram illustrating a closed-loop feedback system according to the invention during an implantation procedure. As shown in FIG. 4, system 70 includes a brain measuring device 72 over the head of patient 71. Brain measuring device 72 measures brain signals and is coupled to brain activity monitoring device 74. Brain activity monitoring device 74 may monitor the brain signals, and may include a therapy indicator gauge 75 to quantify the level of effectiveness of the stimulation therapy.

Brain activity monitoring device 74 communicates (e.g., telemetrically, via wires or via another medium) with an external stimulator 76, which may include the functionality of an implanted stimulator device and a programmer for an implanted stimulator device. The brain signals may be in the form of a sensed EEG, MEG, Electro-Corticography (EcoG), or other neurological signal, which may convey a selected biomarker. External stimulator 76 is electrically coupled to one or more implanted elements 77 (such as electrodes, leads or catheters), and may adjust stimulation parameters (either manually based on clinician adjustments or automatically). Importantly, such stimulation parameter adjustments are based on brain activity, as quantified by brain measuring device 72 and brain activity monitoring device 74, both of which may be external to patient 71. In addition, a physician may use the brain activity, as quantified by brain measuring device 72 and brain activity monitoring device 74 to make informed decisions regarding the placement of one or more elements 77 (such as electrodes, leads or catheters) during the implantation procedure. That is to say, elements 77 are positioned and repositioned based on the brain activity quantified by brain measuring device 72 and brain activity monitoring device 74.

Figure 5:
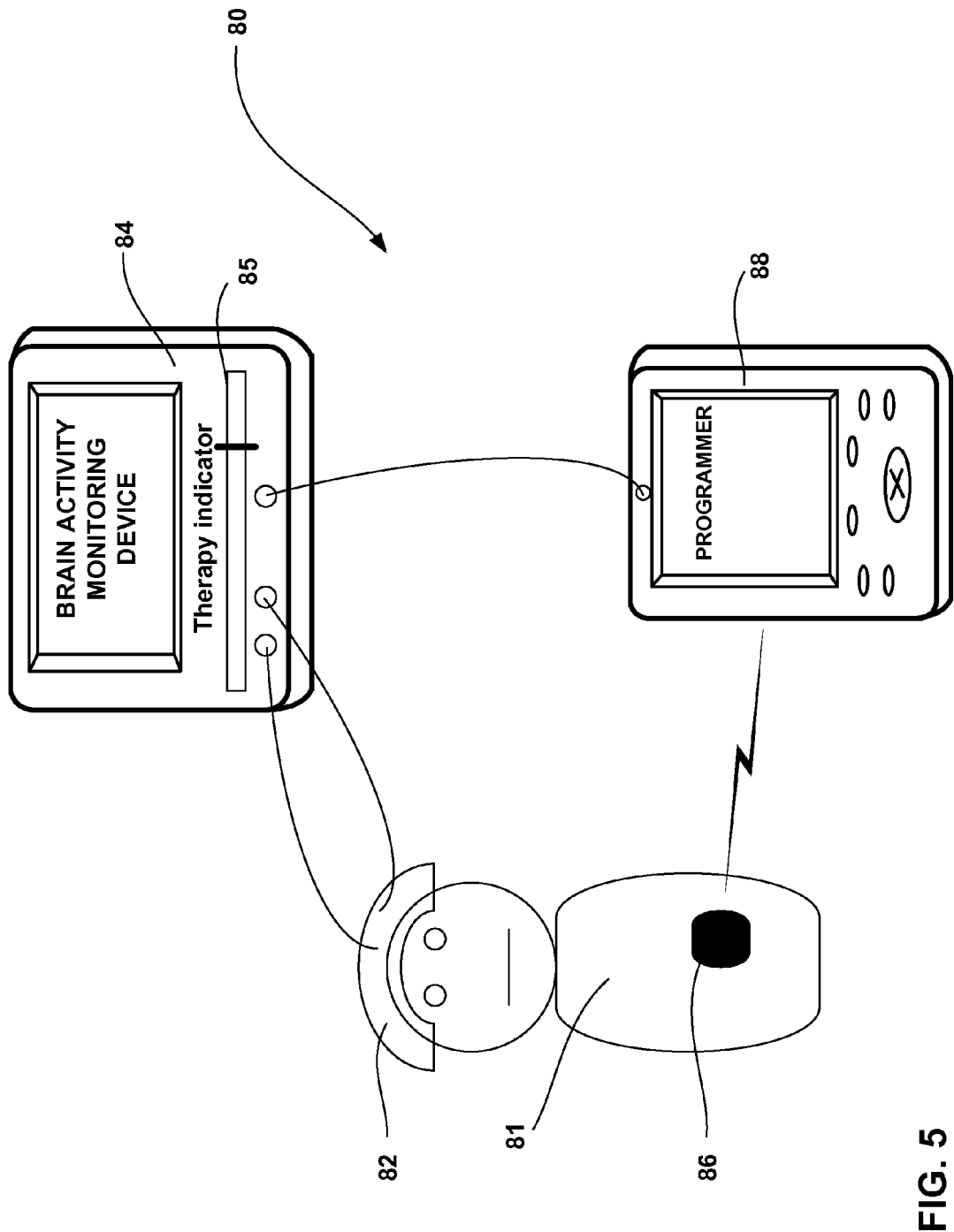
FIG. 5 is a diagram illustrating a closed-loop feedback system following an implantation procedure.

FIG. 5 is a diagram illustrating a closed-loop feedback system following an implantation procedure. A similar system may be used for patient trials. As shown in FIG. 5, system 80 includes a brain measuring device 82 over the head of patient 81. Brain measuring device 82 measures brain signals and is coupled to brain activity monitoring device 84. Brain activity monitoring device 84 may monitor the brain signals, and may include a therapy indicator gauge 85 to quantify the level of effectiveness of the stimulation therapy. Brain activity monitoring device 84 may record the measured brain signals. In some cases, the brain activity monitoring device may also display a patient specific threshold defined by the patient programmer 88 based on subjective feedback from the patient or based on templates of previous patterns of brain activity.

Brain activity monitoring device 84 is coupled to a patient programmer 88, which telemetrically communicates with an implantable medical device 86, which may comprise an implanted electrical stimulator coupled to implanted leads that position electrodes for spinal cord stimulation. Brain activity monitoring device 84 and patient programmer 88 may be coupled via a wire (as illustrated), or via wireless telemetry. Patient programmer 88 may adjust stimulation parameters (either manually based on clinician adjustments or automatically). Alternatively, the implantable medical device may adjust is parameters itself, without the need for a programmer. In any case, importantly, such stimulation parameter adjustments may be based on brain activity (e.g., measured brain signals), as identified and/or quantified by brain measuring device 82 and brain activity monitoring device 84, both of which are external to patient 81. As described herein, patient programmer 88 may use quantified brain activity information to select or adjust sets of electrodes and stimulation parameters in a manner that promotes efficacy of stimulation treatment. In this way, brain activity monitoring device 84 provides direct feedback to patient programmer 88. Patient programmer 88 may then be programmed manually in an automated fashion, e.g., for stimulus parameter selection. Any programming adjustments can then be sent from patient programmer 88 to implantable medical device 86, which may comprise a deep brain stimulator, a spinal cord stimulator, a peripheral nerve stimulator, a drug delivery device, or another type of implantable medical device.

FIGS. 6-9 are different block diagrams illustrating different architectures for implementing algorithms that may implement aspects of the invention. Some or all of the architectures of FIGS. 6-9 may be implemented as circuits or algorithms in a patient programmer (such as patient programmer 88 of FIG. 5), or possibly within an implanted or external stimulation generator or drug pump. The discussion herein regarding a patient programmer may more broadly apply to any external programmer, whether or not it would be characterized as a "patient" programmer. In some cases, for example, the programmer may be used only by a clinician or physical. The term patient programmer is simply used for illustrative purposes.

In the examples of FIGS. 6-9, the patient programmer may receive quantified input of brain activity, process the input, and determine whether stimulation parameter adjustments should be made. If so, patient programmer 88 communicates such adjustments to implantable stimulator 86. However, one or more of the architectures of FIGS. 6-9 may also be implemented in other devices, such as brain activity monitoring device 84 of FIG. 5). In this later case, brain activity monitoring device 84 may processes the measured data and determine whether stimulation parameter adjustments should be made. In this case, brain activity monitoring device 84 may communicate desirable adjustments to patient programmer 88, which can then telemetrically communicate such adjustments to implantable stimulator 86. Alternatively, desirable adjustments could be communicated directly from the brain activity monitoring device 84 to implantable stimulator 86. Some of the architectures of FIGS. 6-9 (such as that of FIG. 6) may be implemented during a trial stage to provide an indicator of whether or not SCS will work for certain patients. Several frequency bands are discussed below, but the invention may not be limited to any specific frequency band. All frequency and power values in the 0-300 Hz range, or possibly other ranges could be assessed in accordance with the invention.

Figure 6:
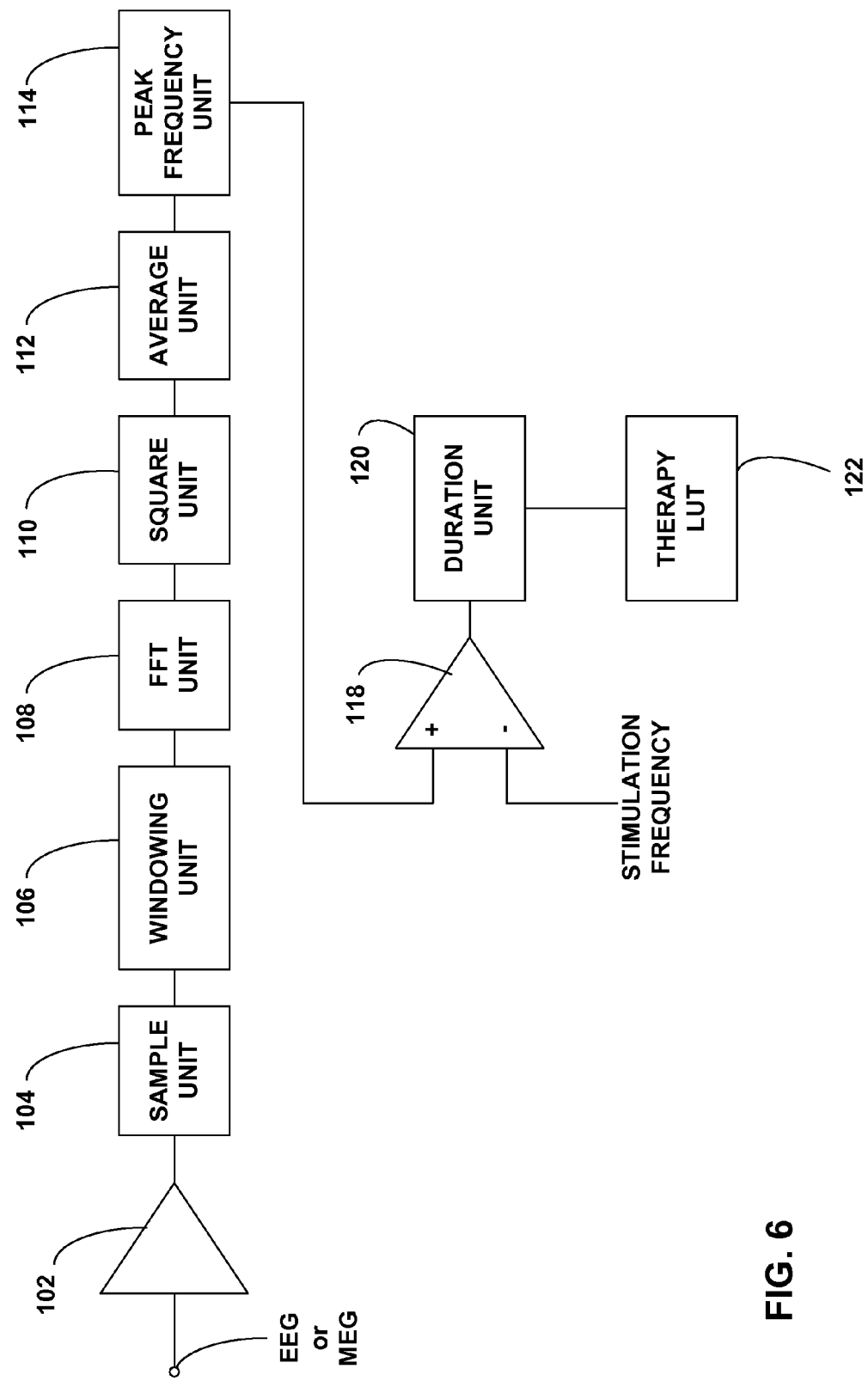
FIGS. 6-9 are different block diagrams illustrating different architectures for implementing algorithms that can adjust stimulation therapy based on detected brain signals.

FIG. 6 illustrates an architecture that includes various units, which may be implemented in hardware, software, firmware, or any combination thereof. In particular, the architecture of FIG. 6 includes an amplifier 102 that receives an EEG or MEG signal as input. The architecture of FIG. 6 also include sample unit 104, window unit 106, fast Fourier transform (FFT) unit 108, square unit 110, average unit 112, stimulation band unit 114, peak frequency unit 116, comparator unit 118, duration unit 120 and a therapy lookup table 122.

Functionally, the algorithm performed by the architecture of FIG. 6 detects the power in the evoked frequency band (e.g., 0-100 Hz), and calculates the total power as well as the frequency at which the maximum power occurred. The detected frequency is compared to the stimulation frequency or harmonics of the stimulation frequency. This comparison can be made using ratios or differences (e.g., the detected divided by the actual or the detected minus the actual). There may also have to be a threshold for maximum power, whereby there may need to be enough power in a particular frequency band in order to have effective SCS. The architecture of FIG. 6 may provide an indicator that SCS will work for certain patients.

More specifically, as shown in FIG. 6, amplifier 102 receives EEG or MEG signals and amplifies or attenuates the signals. Sample unit 104 comprises an analog to digital converter that samples the signals, e.g., at 256 Hz. Windowing unit 106 generates a window of samples from a continuous waveform of samples, and FFT unit 108 performs a fast Fourier transform on the window of samples. Windowing unit 106, for example, may perform hanning or rectangular windowing.

Square unit 110 squares its input to provide a measure of the power associated with the signals, and average unit 112 calculates the average power level for one or more specific frequency bands of the signals. Peak frequency unit 114 determines the peak frequency associated with the signals and feeds this determined peak frequency to comparator logic 118, which compares the peak frequency with a threshold. Duration unit 120 can provide a time constraint to make sure, e.g., that the peak frequency exceeds the threshold for a specified duration of time. If so, therapy parameters or adjustments can be identified from therapy lookup table (LUT) 122 and used to program, re-program or adjust the implantable medical device.

Figure 7:
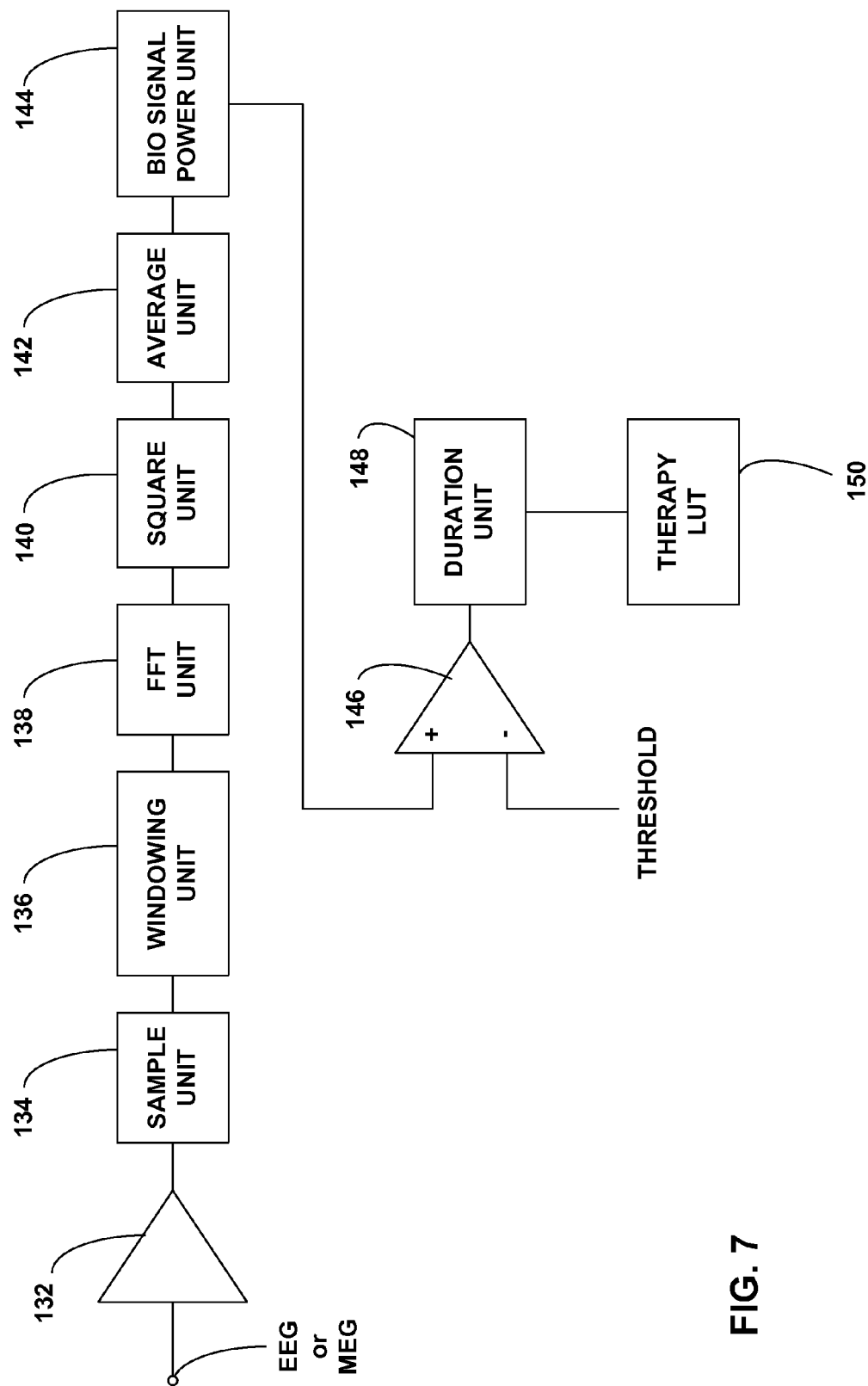
Figure 8:
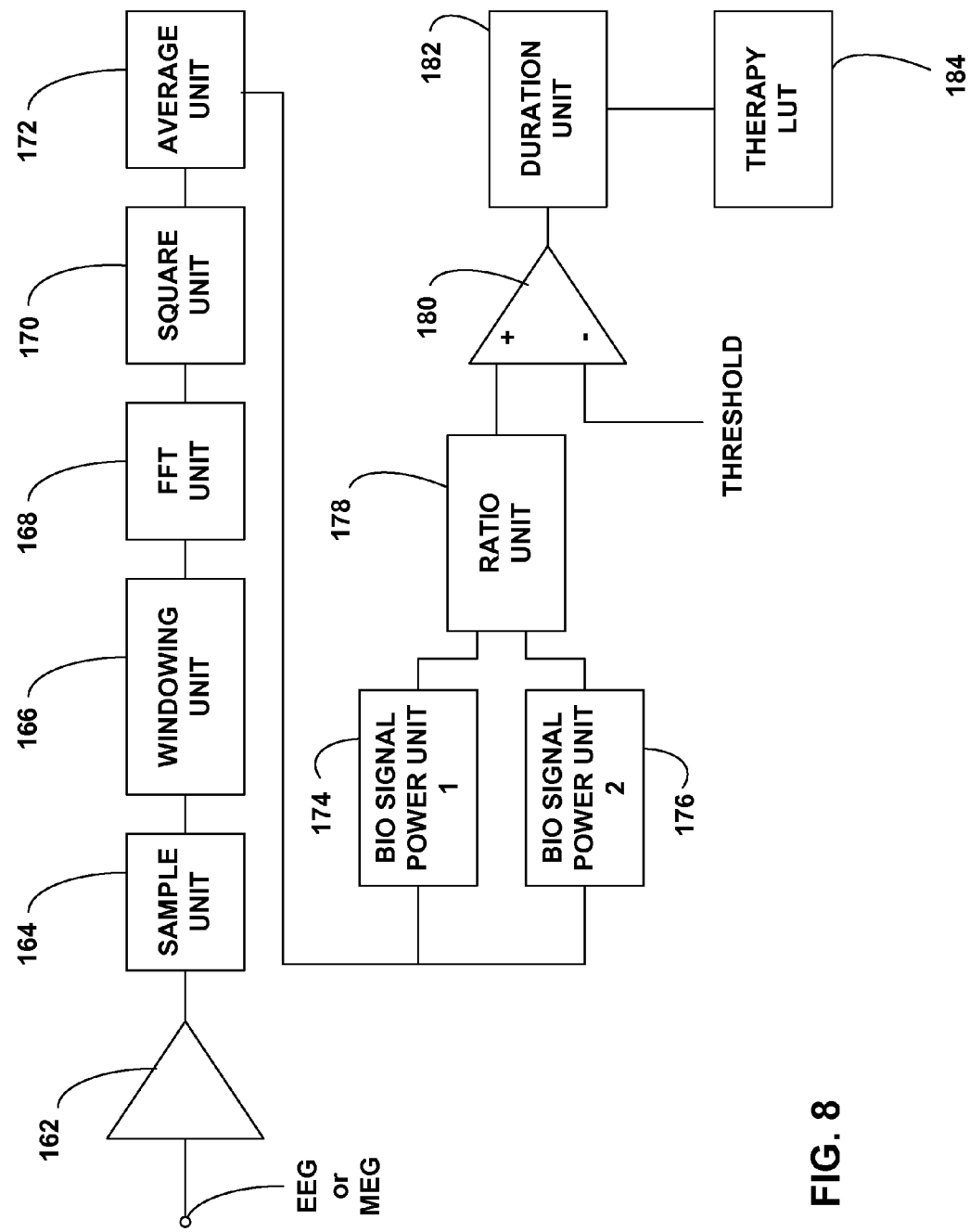

FIGS. 7 and 8 illustrate architectures that include various units, which may be implemented in hardware, software, firmware, or any combination thereof. In particular, the architecture of FIG. 7 includes an amplifier 132 that receives an EEG or MEG signal as input and amplifies the received signal. The architecture of FIG. 7 also include sample unit 134, windowing unit 136, FFT unit 138, square unit 130, average unit 132, bio signal power unit 144, comparator unit 146, duration unit 148 and a therapy lookup table 150.

The functionality implemented by the architecture of FIG. 7 may generally detect the power in a particular frequency band (see Table 1), calculate the sum of the power in that band, and compare it to a threshold. This threshold can be based on average values obtained from normal patients, or patient-specific average values when stimulation is working. If the power is larger than that of the threshold, the algorithm will indicate that therapy is not working optimally and adjustments have to be made. Such adjustments may be telemetrically communicated to an external or implanted electrical stimulator to adjust stimulation parameters or to adjust electrode sets, or may signal to physician to change lead position or manually adjust stimulation parameters.

TABLE 1

| Frequency Band |
| --- |
| Delta (0-4 Hz) |
| Theta (4-8 Hz) |
| Alpha (8-12 Hz) |
| Beta (12-30 Hz) |
| Low Gamma (30-60 Hz) |
| Medium Gamma (60-90 Hz) |
| High Gamma (>90 Hz) |

More specifically, as shown in FIG. 7, amplifier 132 receives EEG or MEG signals and amplifies or attenuates the signals. Sample unit 134 comprises an analog to digital converter that samples the signals. Windowing unit 136 generates a window of samples from a continuous waveform of samples, and FFT unit 138 performs a fast Fourier transform on the window of samples. Like windowing unit 106 of FIG. 6, windowing unit 136 of FIG. 7 may perform hanning or rectangular windowing.

Square unit 140 squares its input to provide a measure of the power associated with the signals, and average unit 142 calculates the average power level for one or more specific frequency bands of the signals. Bio signal power unit 144 determines an amount of power associated with the specific frequency band (e.g., the theta band) feeds this determined power to comparator logic 146, which compares the power a threshold. Duration unit 148 can provide a time constraint to make sure, e.g., that the peak frequency exceeds the threshold for a specified duration of time. If so, therapy parameters or adjustments can be identified from therapy lookup table (LUT) 122 and used to program, re-program or adjust the implantable medical device.

The power signal that is generated by the architecture of FIG. 7 and fed into comparator 146 may comprise an absolute measure of the power within the frequency band of interest. The frequency band of interest may comprise the theta band (4-9 Hz) or possibly other frequency bands. Example frequency bands of interest include the beta band 502 (approximately 7-35 Hz) such as 12-30 Hz, the gamma band (greater than or equal to approximately 30 Hz), a high gamma frequency band (greater than approximately 90 Hz or other frequency ranges, such as between approximately 50-1000 Hz, or between approximately 60-300 Hz.

In some cases, ratios, summations or differences associated with different power bands may be defined and compared to threshold. In the architecture of FIG. 8, the bio signal power of one frequency band (such as the theta band) is compared to the bio signal power of another frequency band (such as the alpha band) to define a ratio that is compared to a threshold. In contrast, in the architecture of FIG. 7 the band power of one particular frequency band is compared to the threshold. The alpha power is typical defined by a state when the patient is relaxed with their eyes closed. Examples of possible biosignals that could be compared are shown in Table 2.

TABLE 2

| Biosignal 1 e.g. | Biosignal 2 e.g. |
| --- | --- |
| Alpha (8-12 Hz) | Delta (0-4 Hz) |
| Alpha (8-12 Hz) | Theta (4-8 Hz) |
| Gamma (>30 Hz) | Delta (0-4 Hz) |
| Gamma (>30 Hz) | Alpha (8-12 Hz) |
| Beta (12-30 Hz) | Theta (4-8 Hz) |

The architecture of FIG. 8 includes an amplifier 162 that receives and amplifies an EEG or MEG signal as input. Like the architectures of FIGS. 6 and 7, the architecture of FIG. 8 also includes a sample unit 164, a windowing unit 166, an FFT unit 168, a square unit 160, and an average unit 172. These signal processing components could be modified or changed in other embodiments. In any case, in FIG. 8, these signal processing components process signals for two different bands so that to different bio power signals can be generated by bio power unit 1 (174) and bio power unit 2 (176). The different power signals generated by units 174 and 176 may comprise power signals in the theta and alpha band, but the invention is not limited to any particular power bands. Ratio unit 178 generates a ratio of the two different power signals from units 174 and 176 and comparator unit 180 compares the ratio to a threshold. Duration unit 182 provides a time constraint to make sure, e.g., that the ratio exceeds the threshold for a specified duration of time. If so, therapy parameters or adjustments can be identified from therapy lookup table (LUT) 184 and used to program, re-program or adjust the implantable medical device.

Again, the functionality implemented by the architectures of FIGS. 7 and 8 may generally detect the power in a particular frequency band (e.g., 4-9 Hz), calculate the sum of the power in that band, compare it to a threshold. This threshold can be based on average values obtained from normal patients, or patient-specific average values when stimulation is working If the power is larger than that of the threshold, the algorithm will indicate that therapy is not working optimally and adjustments have to be made. Such adjustments may be telemetrically communicated to an external or implanted electrical stimulator to adjust stimulation parameters or to adjust electrode sets, or may signal to physician to change lead position or manually adjust stimulation parameters. The comparisons can be made using ratios or differences (detected divided by actual or detected minus actual) or any combination of mathematical operations. In the architecture of FIG. 8, power in one band (such as the theta band) is compared to power in another band (such as an alpha band power) to define a ratio that is compared to a threshold, while in the architecture of FIG. 7 a bio power measurement is simply compared to the threshold.

Figure 9:
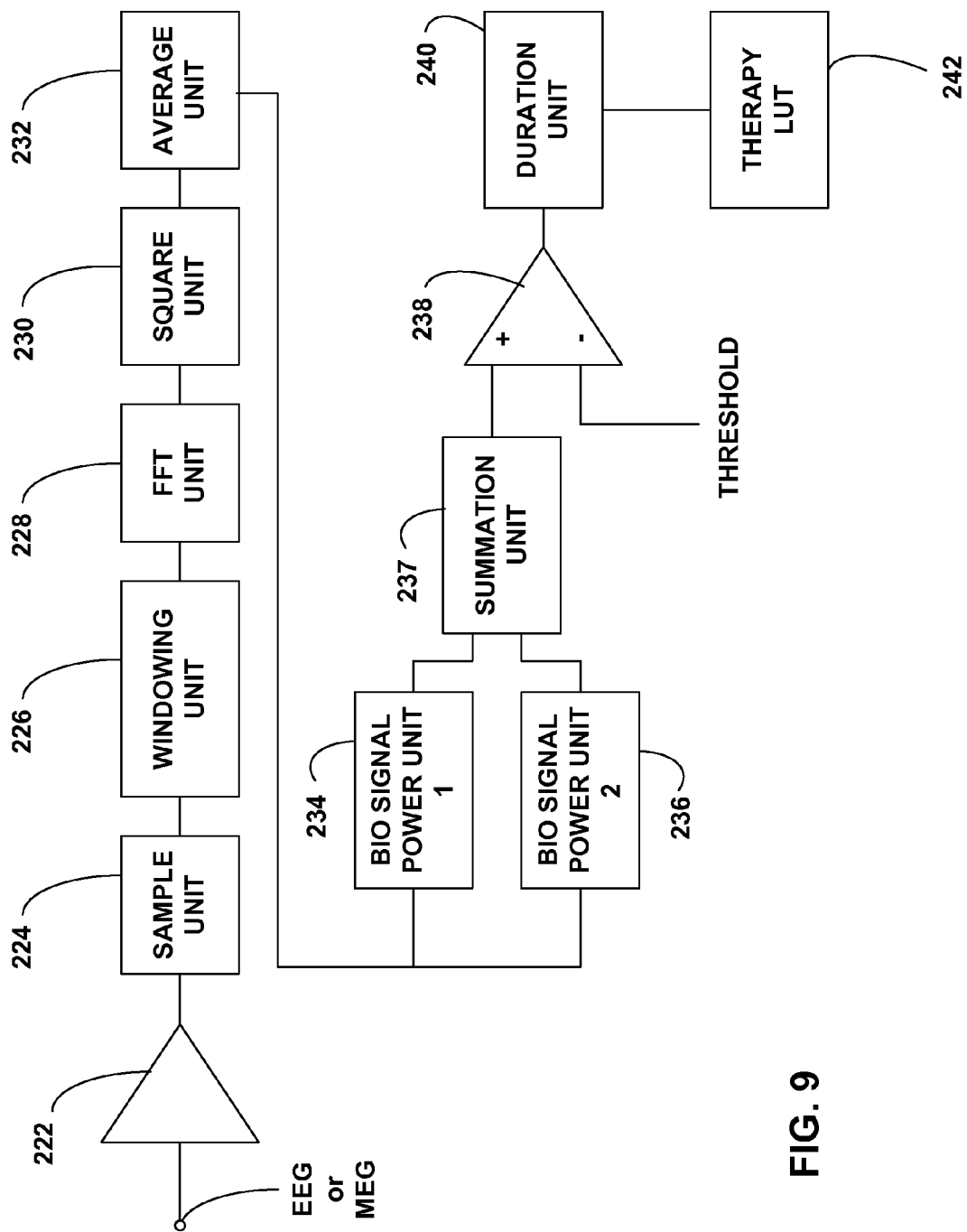

FIG. 9 illustrates yet another architecture that is similar to those of FIGS. 6-8 in many respects. The various units of FIG. 9 may be implemented in hardware, software, firmware, or any combination thereof. The architecture of FIG. 9 includes an amplifier 222, a sample unit 224, a windowing unit 226, an FFT unit 228, a square unit 230, an average unit 232, two different bio power units (234 and 236), a summation unit 237, a comparator unit 238, a duration unit 240 and a therapy lookup table 242. The architecture of FIG. 9 operates in the same was as that of FIG. 8, but uses a summation of two different power signals (via summation unit 237) rather than a ratio. The summation may be weighted in some cases. The summation is compared to a threshold (via comparator unit 238) and duration unit 240 applied a timing constraint. If the summation exceeds the threshold for enough time, adjustments to the implantable medical device can be identified from therapy LUT.

In healthy patients, gamma band power may correlate with the subjective perception of pain. The functionality implemented by the architectures shown in FIG. 9 detects the power in two or more specific bands, calculates the sum of the power in those bands, and compares it to a threshold. If the power is larger than that of the threshold, this can indicate that therapy is not working optimally and adjustments should be made, such as an increase or decrease in amplitude, pulse width or pulse rate. Such adjustments may be telemetrically communicated to external or internal electrical stimulator to adjust stimulation parameters or to adjust electrode sets, or may signal to physician to change lead position or manually adjust stimulation parameters. Examples of two frequency bands whose power can be summated are shown in Table 2.

Again, the different comparisons may be performed based on ratios of power in different bands, sums of power in different bands, differences in power of different bands, and so forth. The various embodiments described here include an external device that monitors brain signals and indicates therapy status. However, other embodiments are envisioned. The invention may record brain signals from bone screws to achieve better signal to noise ratio. Such bone screws are still considered to be an external brain monitoring mechanism. The invention may also implement a closed loop implantable device. Once a patient is selected for successful SCS, therapy may be monitored (from brain sensors) and communicated via telemetry to stimulation device to adjust stimulation parameters (e.g., by going through an algorithm for stimulus parameter search based on brain feedback).

In some cases, brain sensing can be made from two or more locations on the head or scalp and the difference or ratio of power in two locations can help predict therapy status. For example, somatosensory and anterior cingulate cortices (ACC) may be sensed to detect maximal change in affective component of pain (over anterior cingulate). If the band power is greater over ACC, then perception of a painful state would likely be augmented, and stimulation or an increase in stimulation intensity may be useful to alleviate such pain. In addition, brain sensing may rely on power ratios between different frequency bands as a biomarker.

The invention may contemplate adaptive stimulation. In this case, an algorithm may consider the rate of change of relative band power, possibly in addition to the already mentioned ratios or differences in power between two or more frequency bands. For example, if the power in one band or power between two or more frequency bands is changing at too high of a rate, it may be necessary to trigger stimulation before threshold detection in order to account for any time delays in the responsive stimulation. On the other hand, if the power is changing slowly, the trigger of stimulation may be less critical. The algorithm may store rate of change data, and learn from previous trials to determine when to trigger stimulation.

Rates of change of power may also be taken into account when designing the stimulus parameters algorithm timing in order to make sure that the brain response is adequately processed. For example, the rate of change of power may be compared to one or more rate thresholds to determine whether adjustments should be made. Stimulation should occur for enough time to detect the brain response. That is, any changes to the stimulation should be allowed to take effect for enough time that the brain response can be accurately determined.

When trying to find optimal or desirable stimulation parameters for a system like that of FIG. 4 or 5, the electrode configuration, pulse width, amplitude, and frequency may be adjusted. If brain patterns associated with pain are still present, the set of electrodes activated may be changed until a desirable configuration is found.

Alternatively, if pain therapy in an implanted system is lost due to lead migration, or if the pain pattern changes, the device may reestablish therapy using a different set of electrodes based on brain signal feedback. These changes may occur automatically in a closed loop fashion, or may require clinician authorization and adjustment via manual changes using the programmer.

Figure 10:
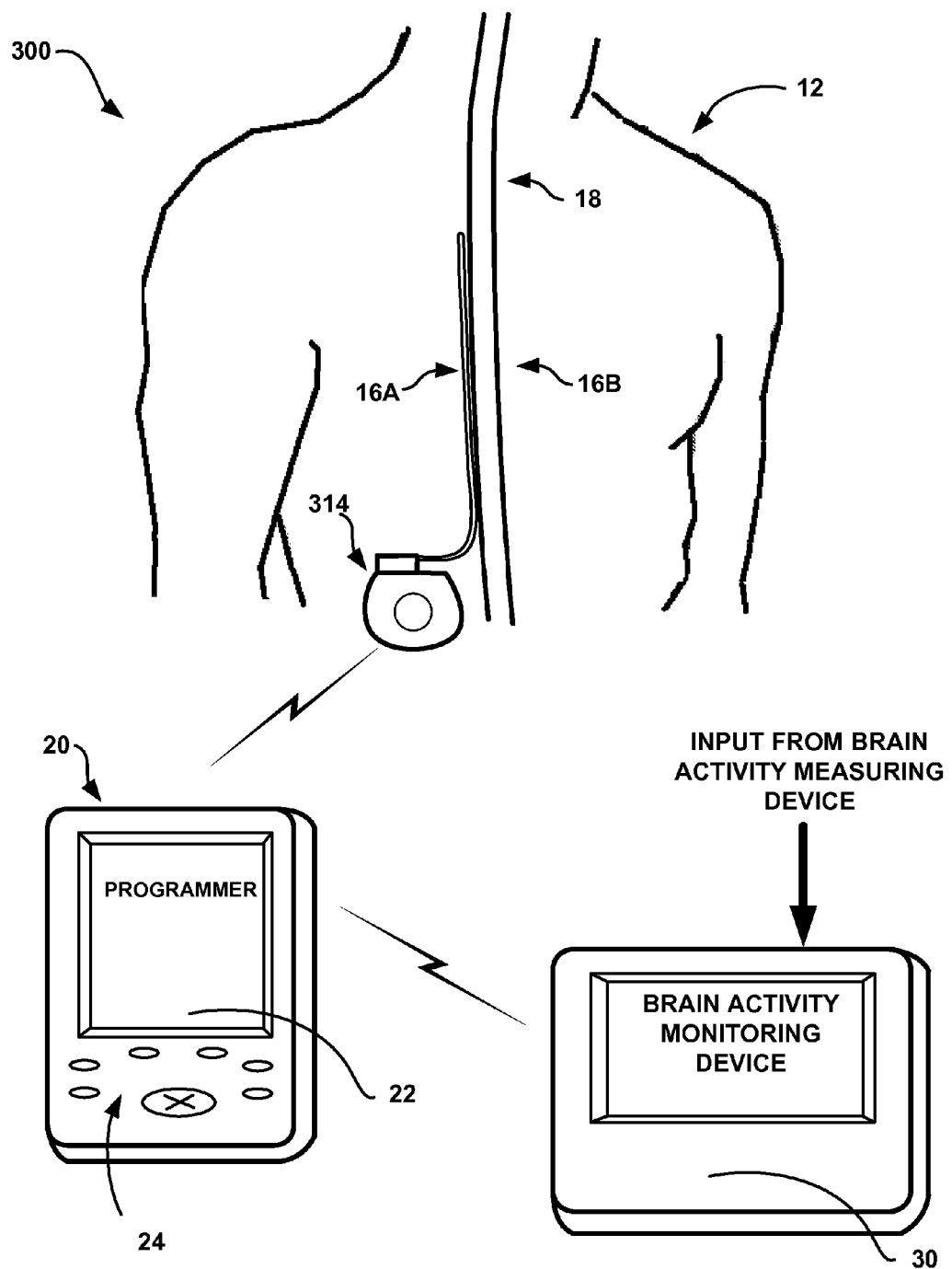
FIG. 10 is a diagram illustrating an example system for programming and delivering drug therapy to a patient based on detected brain signals.

FIG. 10 is a diagram illustrating an example system for programming and delivering drug therapy to a patient based on detected brain signals. The system of FIG. 10 is very similar to that of FIG. 1, but includes an implanted drug pump 314 instead of an implanted pulse generator. In this case, therapy provided by implanted drug pump 314 is adjusted based on the response of the brain of patient 12.

Figure 11:
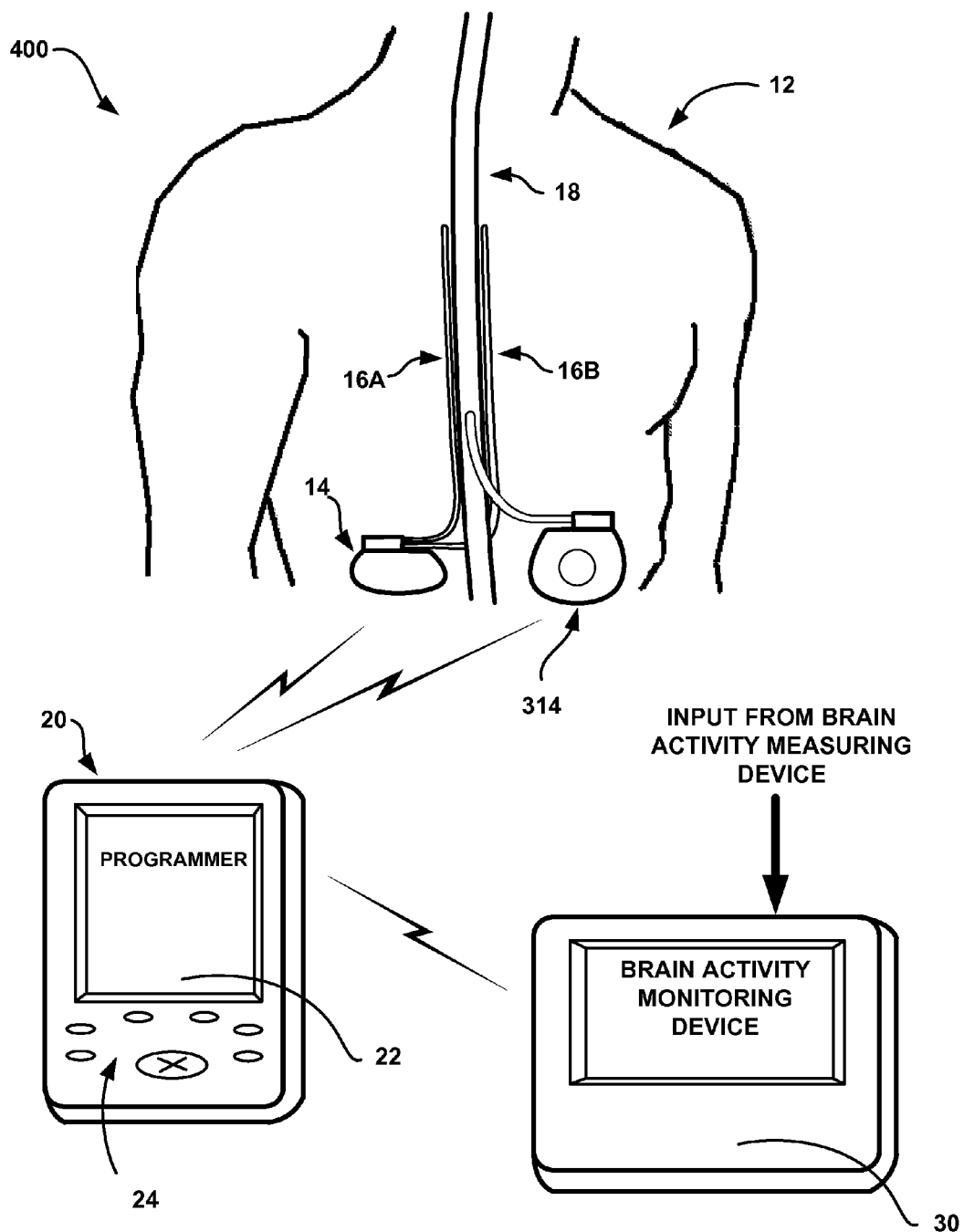
FIG. 11 is a diagram illustrating an example system for programming and delivering stimulation therapy and drug therapy to a patient based on detected brain signals.

FIG. 11 is a diagram illustrating an example system for programming and delivering drug therapy and electrical stimulation therapy to a patient based on detected brain signals. The system of FIG. 11 is very similar to that of FIGS. 1 and 10, but includes both an implanted drug pump 314 and an IMD 14 in the form of an implanted pulse generator. In this case, therapy provided by implanted drug pump 314 and IMD 14 is adjusted based on the response of the brain of patient 12.

Figure 12:
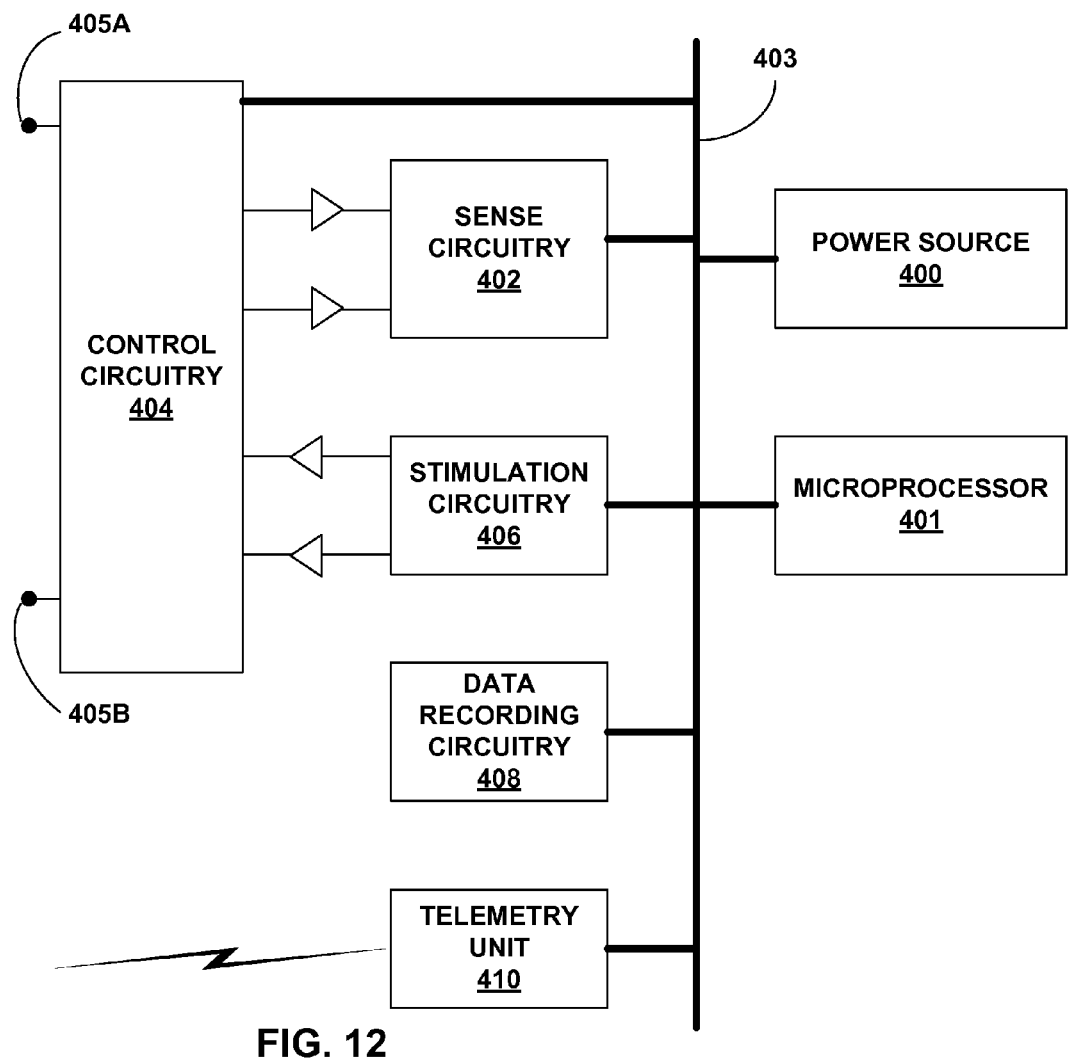
FIG. 12 is a block diagram of an exemplary implantable medical device that may be used in accordance with the techniques described herein.

FIG. 12 is a block diagram of an exemplary implantable medical device that may be used in accordance with the techniques described herein. An implantable medical device may include some or all of the illustrated elements of FIG. 12, as described in greater detail below. The embodiment shown in FIG. 12 is illustrated as including sense circuitry 402, which may supplement the external brain sensing described herein. In most cases according to the invention, however, it may be desirable for an implantable medical device to eliminate sense circuitry 402 in favor of the external brain sensing described herein, as internal electrodes for brain sensing may require invasive surgery.

A power source 400 may be either a primary battery or a rechargeable battery, for example, with a recharge coil. A battery provides a source of electrical energy to power the electronics, and to power any electromechanical devices (e.g., valves and pumps) that may be associated with therapy delivery (e.g., medicament delivery and/or electrical stimulation).

Sense circuitry 402 may include EEG amplification, filtering, and biomarker processing circuitry. Filtering, for example, may include bandpass filters for identifying and/or measuring signals in different frequency ranges of interest (e.g., the beta and gamma bands). Bandpass filters may be analog or digital, and may include low-pass and high-pass filters. Biomarker processing may include, for example, circuitry (e.g., microprocessors and/or digital signal processors) for performing computations (e.g., FFT analysis, ratio calculations, etc.). Again, sense circuitry 402, although illustrated in FIG. 12, would typically be eliminated for most embodiments of an implantable medical device according to this disclosure, insofar as brain sensing according to the invention is performed external to the patient. Microprocessor 401 is illustrated in FIG. 12 and may be invoked to perform the calculations described herein. The various components of FIG. 12 may be coupled via a data communication bus 403.

Control circuitry 404 may include timing, parameter setting, and switching and blanking circuitry. This may include, for example, circuitry that determines the order and speed of input signal acquisition from a number of sources (e.g., multiplexing). During electrical stimulation therapy, for example, blanking circuitry may be employed to avoid false sensing of stimulation signals and/or to protect sensing circuitry. In any case, control circuitry may drive electrodes 405A and 405B to provide the stimulation pulses to a patient.

Programmable parameter settings may include, for example, the ability to modify the frequency range or ranges of interest, as well as the calculation of the biomarker itself. Stimulation circuitry 406 may include generator circuits for electrical stimulation and/or pump control circuits for drug delivery. Data recording circuitry 408 may include memory for storing acquired signals and detected events. Telemetry unit 410 may provide the ability to communicate, for example, providing the ability to program device settings/ parameters, to retrieve stored data, and/or to stream received data to an external monitor (e.g., in real-time). An implantable medical device may include mechanical packaging such as a biocompatible and hermetically sealed case to house the components shown in FIG. 12, and may also include one or more connectors, a drug pump, and feedthroughs (e.g., electrical and mechanical).

In some embodiments, an implantable device may be adapted to deliver therapy in an open-loop mode (e.g., on a periodic basis or for monitoring), a closed-loop mode (e.g., in response to a biomarker), or a combination of open-loop and closed-loop modes. In the case pain therapy, closed-loop therapy may be adjusted (either automatically or manually) in response to measured levels of two biosignals. Therapy delivery based on measured levels of oscillatory activity in specific frequency bands may also be beneficial to patients with certain other disorders.

In one embodiment, closed-loop therapy may be delivered and adjusted by an implanted device, for example, in response to a biomarker determined from the externally measured levels of oscillatory signals in specific frequency bands. One such biomarker may be determined from a ratio of signal energy of two different frequency bands, for example. Oscillatory activity (e.g., signal energy) may be quantified in terms of measured signal power (e.g., micro-volts$^2$, as shown in FIG. 3), or may be quantified as a relative power (e.g., as a percentage of signal power within a given frequency band to the overall signal power), using fast Fourier transform (FFT) techniques, for example. In further embodiments, closed-loop therapy may involve adjusting therapy delivery parameters (e.g., frequency, amplitude, location, drug type, amount, etc.) in order to maintain the measured biomarker within some pre-determined (and/or possibly patient-specific) range of values, for example. In addition to a ratio of signal energies, other biomarkers may be defined that compare signal activity in frequency bands of interest, e.g., as power ratios, or which compare signal activity in various locations, for example. For example, average and/or peak signal power levels, Q factor values (indicative of the rate of energy dissipation relative to the oscillation frequency), and other methods of quantifying the oscillations in two or more frequency bands, may be used as first and second values from which calculate ratios, difference signals, squared difference values, etc.

In some embodiments, an open-loop therapy mode may be provided which allows an operator (e.g., a physician) to review measured levels of signals in two or more frequency bands and make adjustments to therapy delivery based thereon. In one embodiment, an operator may retrieve biomarker values determined from signals in two or more frequency bands, and use the biomarker values to make adjustments to therapy delivery. Such adjustments may include changes to the programmed therapy delivery settings of an implantable device, for example.

In other embodiments, an implantable medical device or system may provide the ability to store information regarding frequency related oscillatory signals over relatively long periods of time to provide an operator with trending information, for example, to evaluate the effectiveness of therapy over time. The stored information may include one or more biomarkers for evaluating and treating pain.

Trending information may include, for example, statistical snapshots of data taken over a defined window of time. For example, during a 5 minute window of time, information regarding oscillatory signals may be summarized into one or more statistical measures. A mean value for the 5 minute window is one example. A median is another. A series of three values may be stored for each 5 minute window, comprising a $6^{th}$ percentile value, a $50^{th}$ percentile value, and a $94^{th}$ percentile value, for example. Such a trending technique may, for example, greatly reduce the memory requirements of an IMD, while retaining useful trending information. The window period and/or the types of statistical measures used could be user-selectable, e.g., by a physician or clinician, or possibly by the patient.

Various modes of operation (e.g., open-loop and closed-loop) may provide data storage capabilities (e.g., recording and/or trending of data received), or may allow for the selection of a non-storage mode (e.g., response to measured signals and programmed settings, but without data storage). For example, a closed-loop therapy mode, once properly programmed for a particular patient, may have data storage disabled to minimize processing and power demands on a device. Telemetry of data may also be a feature of certain modes of operation, with or without data storage. For example, an open-loop mode may be initiated to allow for testing of programmed settings and/or to determine optimal settings via physician control. Real-time telemetry may be employed during such testing and programming, and data storage associated with such testing may or may not be turned off, depending on physician preference.

Again, external or implanted sensors may be used to measure EEG signals to determine a biomarker. Examples of methods of determining a biomarker in accordance with embodiments of the invention are outlined in the block diagram of FIG. 14. Externally measured EEG signals may be filtered into two discrete frequency bands corresponding to biomarkers in two frequency bands. This is shown in the time domain algorithm 500 by using bandpass filters (including low-pass and high-pass filters) corresponding to specific frequency bands (see Table 2 for examples of frequency bands). This may be accomplished by using analog bandpass filters, or by sampling and using digital bandpass filters, or by sampling and performing time domain-to-frequency domain conversion, or by combinations of these and other methods known to those of ordinary skill in the art. The bandpass filter (or filters) corresponding to the beta band, for example, may define other frequency ranges, such as approximately 11-30 Hz, in some embodiments. Similarly, the bandpass filter (or filters) corresponding to the gamma band, for example, may define other frequency ranges, such as approximately 50-1000 Hz, or approximately 60-300 Hz, in certain embodiments.

In the frequency domain algorithm 550, a fast Fourier transform (FFT 552 may be applied to the input signal (after appropriate sampling and windowing, for example) to obtain the beta band 554 and gamma band 556 information.

Each of these output signals is processed through an energy averaging algorithm and a comparison of the two biosignals is made. In certain embodiments, the comparison may include calculation of the ratio of a first frequency band signal energy to a second frequency band signal energy (or vice versa). The output ratio may then be used to assess efficacy of pain treatment, and/or may be compared to a reference value (e.g., a threshold) to assess the efficacy of pain treatment. The comparison of the ratio value to a predetermined threshold may, for example, provide a signal to adjust therapy delivery accordingly, e.g., by adjusting one or more therapy parameters such as amplitude, pulse rate, or pulse width, or dosage, rate, or duration, as applicable. This may, for example, involve the use of a therapy lookup table according to some embodiments, or may involve a logic function or calculation.

An external instrument (such as the patient programmer described above) may be used for programming the implanted device, viewing device status, and uploading recorded data, for example. It may typically be a computing platform with a graphical user interface that can communicate via telemetry with the implanted device. A communication link may be established that is short range (less than 1 foot), or long range (greater than 1 foot). Short-range telemetry may require a telemetry head, which can be tethered or wireless. Software on the computing platform may be adapted to enable management of device parameters. Many other techniques and architectures could be used, consistent with this disclosure, to obtain brain signals and various biomarkers.

Figure 13:
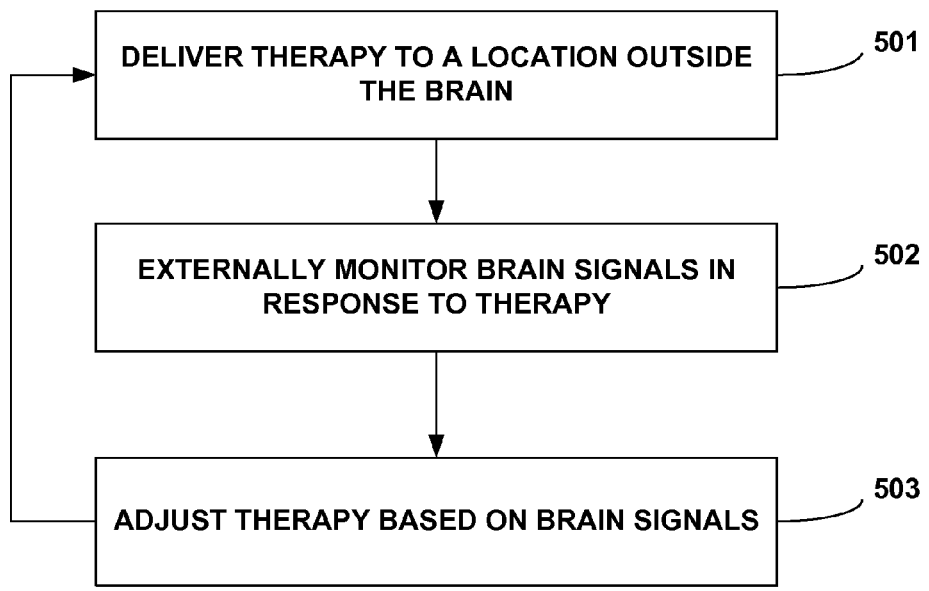
FIGS. 13-15 are flow diagrams illustrating techniques consistent with the invention.

FIG. 13 is a flow diagram illustrating techniques consistent with the invention. As shown in FIG. 13, IMD 14 delivers therapy to a location outside of the brain of patient 12 (501). Brain monitoring device 30 externally monitors brain signals (e.g., from externally measured data from an external brain measuring device) in response to the therapy (502). Programmer 20 then adjusts the therapy based on brain signals (503). Brain monitoring could, alternatively or additionally, be done via implanted brain sensors that communicate with IMD 14 or an external stimulator via wires or telemetry.

Figure 14:
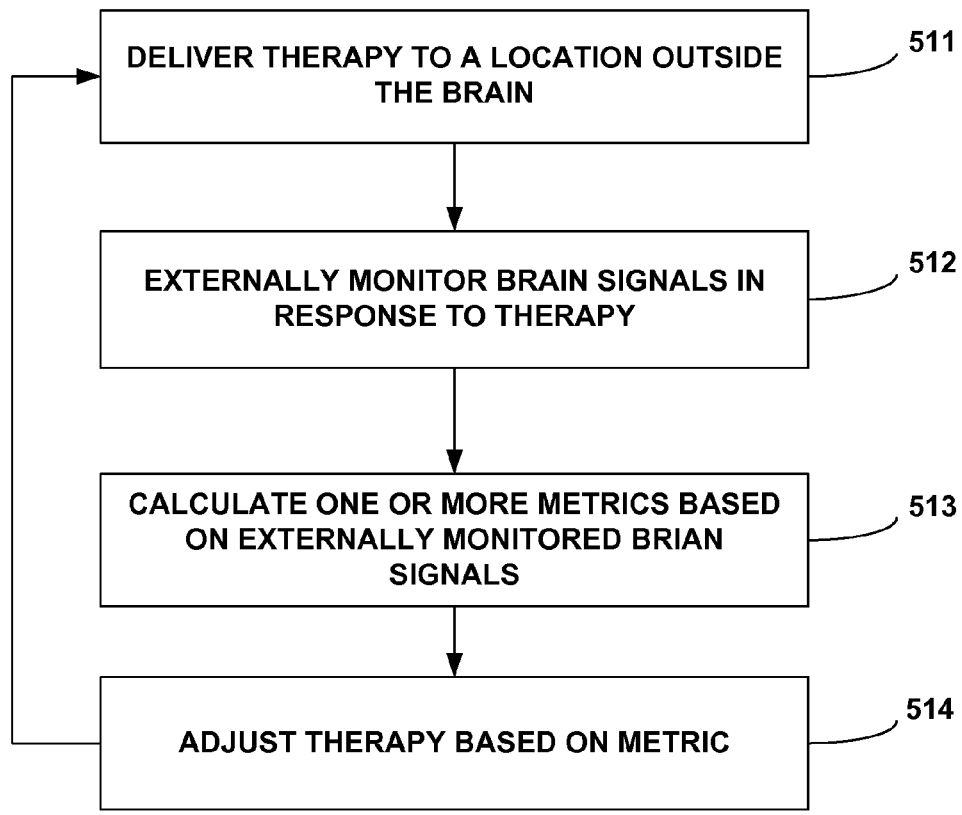

FIG. 14 is another flow diagram illustrating a technique consistent with this disclosure. In this case, IMD 14 delivers therapy to a location outside of the brain of patient 12 (511), and brain monitoring device 30 externally monitors brain signals (e.g., from externally measured data from an external brain measuring device) in response to the therapy (522). Brain monitoring device 30 or programmer 20 calculates one or more metrics based on the externally monitored brain signals (513). The metrics may comprise bio signals, such indications of power in one or more frequency bands, ratios, summations, differences, or other types of metrics that may be generated based on measured brain signals. In this case, programmer 20 then adjusts the therapy based on the metrics (514).

Figure 15:
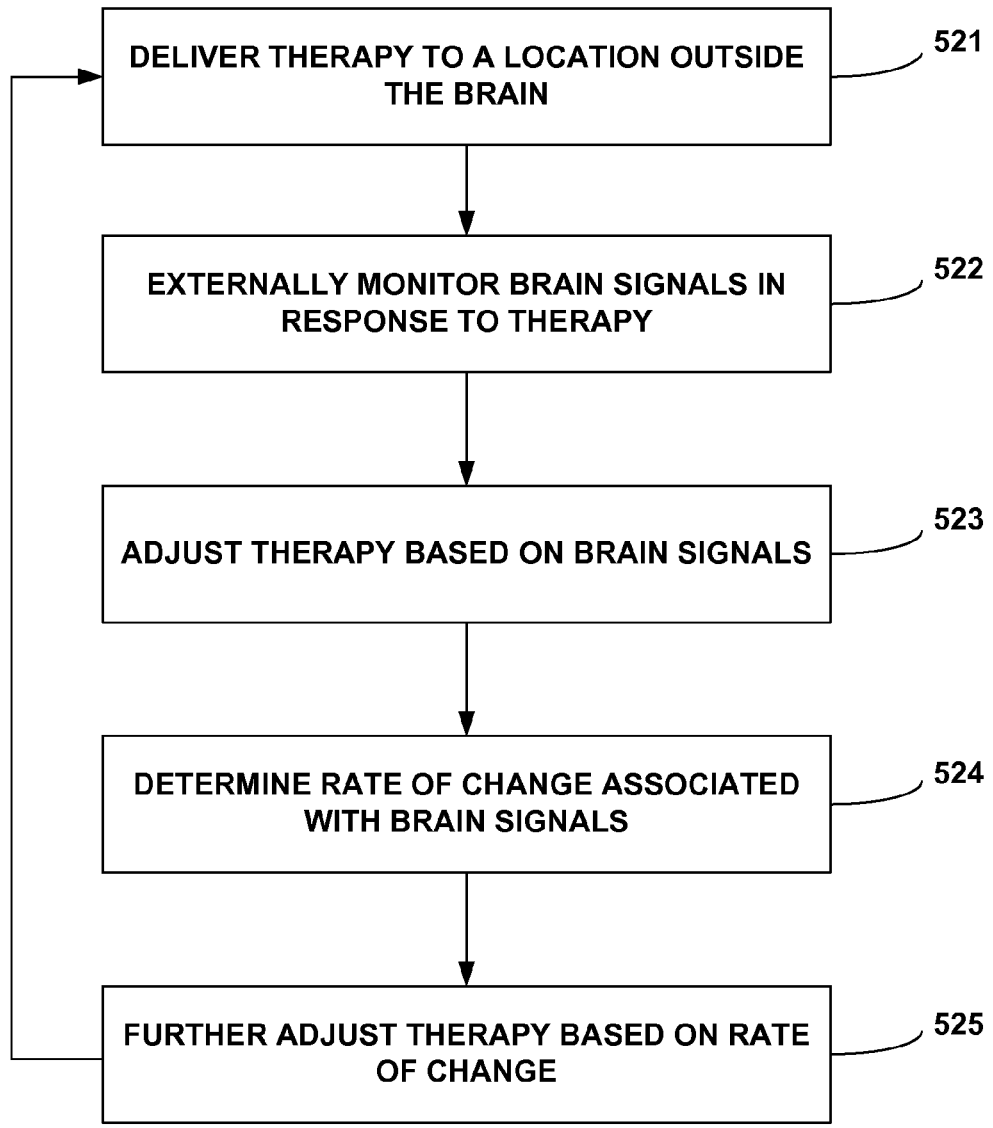

FIG. 15 another flow diagram illustrating a technique consistent with this disclosure. In this case, IMD 14 delivers therapy to a location outside of the brain of patient 12 (521), and brain monitoring device 30 externally monitors brain signals (e.g., from externally measured data from an external brain measuring device) in response to the therapy (522). Programmer 20 then adjusts the therapy based on brain signals (523), possibly using a metric (such as power measure, ratios of power, summations of power, differences of power, or the like) as outlined herein. After adjusting therapy, in this embodiment, brain monitoring device 30 (or possibly programmer 20) then determines a rate of change associated with the brain signals (524), and programmer 20 further adjusts the therapy based on the rate of change (525).

A method according to the invention may comprise monitoring brain signals of a brain via an external brain activity monitoring device, and adjusting electrical stimulation delivered via one or more implanted electrodes to one or more locations outside of the brain based on the brain signals.

The electrical stimulation may be formulated to alleviate pain, and the method may further comprise monitoring the brain signals in a frequency band, such as between approximately 4 and 9 hertz (see also Table 1 for possible frequency bands), and adjusting the electrical stimulation to reduce the brain signals in the frequency band. Alternatively, the method may further comprise monitoring the brain signals in a frequency band, such as between approximately 4 and 9 hertz (see also Table 1 for possible frequency bands), and adjusting the electrical stimulation to increase the brain signals in another frequency band above approximately 9 hertz. In these or other ways, monitored brain signals may facilitate informed adjustments to electrical stimulation therapy to affect (i.e., increase or decrease) brain signals in one or more frequency bands.

In yet another example, the method may further comprise monitoring the brain signals in two or more different frequency bands, determining a ratio of the signals in two or more different frequency bands, and adjusting the electrical stimulation to adjust the ratio in a manner that alleviates the pain. Also, the method may further comprise monitoring the brain signals in one or more frequency bands, adjusting the electrical stimulation to adjust the brain signals, determining a rate of change of the brain signals in response to the adjustments to the electrical stimulation, and further adjusting the electrical stimulation based on the determined rate of change.

In some cases, adjusting the electrical stimulation may comprise adjusting an implantation location of one or more electrodes on the one or more medical leads. In other cases, adjusting the electrical stimulation may comprise selecting different electrodes to be active on the one or more medical leads. In addition, adjusting the electrical stimulation may comprise adjusting one or more stimulation parameters selected from a group consisting of pulse polarity, pulse voltage amplitude, pulse current amplitude, pulse pattern (e.g., random, regular, or other), waveform shape, pulse rate, and pulse width.

The method according to the invention may further comprise measuring the brain signals via a brain measuring device positioned on or attached to a head of a patient, monitoring the brain signals via the external brain activity monitoring device coupled to the brain measuring device, and adjusting the electrical stimulation delivered via one or more implanted electrodes based on the brain signals via an external stimulator coupled to the brain measuring device during implantation of the electrodes.

In another example, the method according to the invention may further comprise measuring the brain signals via a brain measuring device positioned on or attached to a head of a patient, monitoring the brain signals via the external brain activity monitoring device coupled to the brain measuring device, and adjusting the electrical stimulation delivered by an implanted medical device via one or more implanted electrodes based on the brain signals via a programmer coupled to the brain measuring device, wherein the programmer telemetrically communicates with the implanted medical device.

In another example, the method according to the invention may further comprise measuring and monitoring the brain signals via a brain measuring and monitoring device positioned on or attached to a head of a patient, and adjusting the electrical stimulation delivered by an implanted medical device via one or more implanted electrodes based on the brain signals via a programmer coupled to the brain measuring and monitoring device, wherein the programmer telemetrically communicates with the implanted medical device.

In another example, the method according to the invention may further comprise adjusting drug delivery via an implanted drug pump based on the brain signals. In an alternative example, a method according to the invention may comprise monitoring brain signals via an external brain activity monitoring device, and adjusting drug delivery to one or more locations outside of the brain via an implanted drug pump based on the brain signals.

Systems according to the invention may include the described components used to implement the methods described herein. For example, a system according to the invention may comprise an external brain activity monitoring device that monitors brain signals of a brain of a patient, one or more implanted electrodes that deliver electrical stimulation to one or more locations outside of the brain, and a stimulator device that generates the electrical stimulation delivered by the implantable medical leads, wherein the stimulator device adjusts the electrical stimulation based on the brain signals.

In some cases, the electrical stimulation is formulated to alleviate pain, wherein the external brain activity monitoring device monitors the brain signals in a specific frequency band, such as between approximately 4 and 9 hertz, and the stimulator device adjusts the electrical stimulation to reduce the brain signals in the frequency band.

In other cases, wherein the electrical stimulation is formulated to alleviate pain, the external brain activity monitoring device monitors the brain signals in a specific frequency band, such as between approximately 4 and 9 hertz, and the stimulator device adjusts the electrical stimulation to increase the brain signals in another frequency band above approximately 9 hertz.

In other cases, wherein the electrical stimulation is formulated to alleviate pain, the external brain activity monitoring device monitors the brain signals in two or more different frequency bands, and determines a ratio of the signals in two different frequency bands, and the stimulator device adjusts the electrical stimulation to adjust the ratio.

The system according to the invention may further comprise a brain measuring device configured to be positioned on or attached to a head of the patient, wherein the external brain activity monitoring device is coupled to the brain measuring device, and wherein the stimulator device comprises an external stimulator coupled to the brain measuring device during implantation of electrodes.

Also, the system according to the invention may further comprise a brain measuring device configured to be positioned on or attached to a head of the patient, and a programmer, wherein the external brain activity monitoring device is coupled to the brain measuring device, wherein the stimulator device comprises an implantable medical device, and wherein the programmer is coupled to the external brain activity monitoring device and telemetrically communicates with the implantable medical device.

In addition, the system according to the invention may further comprise a programmer, wherein the external brain activity monitoring device comprises a brain measuring and monitoring device positioned on or attached to a head of a patient, wherein the stimulator device comprises an implantable medical device, and wherein the programmer is coupled to the brain measuring and monitoring device and telemetrically communicates with the implantable medical device.

Also, the system according to the invention may further comprise an implantable drug pump that adjusts drug delivery based on the brain signals. As described above, in some cases, the system may form an automated closed loop system in which the stimulator device automatically adjusts the electrical stimulation based on the sensed brain signals.

As an added embodiment, the invention also contemplates a system comprising an external brain activity monitoring device that monitors brain signals of a brain of a patient, and an implantable drug pump that delivers drugs to a location outside of the brain, and adjusts drug delivery based on the brain signals. In this case, the system may also form an automated closed loop system in which the implantable drug pump automatically adjusts drug delivery based on the brain signals.

Also, this disclosure contemplates use of brain monitoring techniques via an implantable sensor that is coupled to or communicates by wireless telemetry with the implantable pulse generator or external pulse generator. In this case, the brain monitoring discussed above would be performed by an implanted sensor. Furthermore, this disclosure also contemplates stimulation directly to the brain (based on measured brain response) in order to alleviate pain.

The invention, in other aspects, may involve external or implantable devices or combined devices. For example, an external pulse generator or external drug pump may be coupled to percutaneously implanted catheter or leads, at least on a temporary trial basis and sometimes longer, although full implantation is preferred for chronic use. The invention may also use either external brain sensing (as primarily described above) or implantable brain sensing. A person could have a brain electrode or electrode array that is coupled via a lead to an SCS IPG, or which transmits signals by wireless telemetry. The invention may also implement a deep brain stimulation device that delivers therapies for pain.

As an added embodiment, the invention may involve a method comprising monitoring brain signals of a brain, and adjusting electrical stimulation delivered via one or more implanted electrodes based on the brain signals to alleviate pain to a patient. The electrical stimulation may comprise neurostimulation such as spinal cord stimulation (SCS), provided to one or more locations outside of the brain. Monitoring the brain may comprise monitoring the brain via an external brain activity monitoring device, or monitoring the brain via an implanted sensor positioned on or in the brain.

Various embodiments of the invention have been described. Aspects of these techniques may be implemented in hardware, software or firmware. If implemented in software, such aspects of the invention may be embodied in a computer-readable medium. In this case, the computer-readable medium may store instructions that upon execution in a processor case the processor to perform one or more aspects of the techniques described above. However, one skilled in the art will appreciate that various additions and modifications can be made to these embodiments without departing from the scope of the invention.

Although various functions have been described as being performed by particular devices, units or modules, in other cases, similar functions may be performed by different devices, units or modules. These and other embodiments are within the scope of the following claims.

The invention claimed is:

1. A method comprising:
 delivering electrical stimulation to a patient via one or more electrodes of a medical device, wherein the one or more electrodes are positioned proximate to a spinal cord of the patient and the electrical stimulation is formulated to alleviate pain in the patient;
 monitoring brain signals of a brain of the patient in a gamma frequency band via an external brain activity monitoring device; and
 adjusting the electrical stimulation delivered via the one or more electrodes based on the brain signals.

2. The method of claim 1, wherein the one or more electrodes are disposed on one or more implanted medical leads.

3. The method of claim 1, the method further comprising: adjusting the electrical stimulation to affect the brain signals in the gamma frequency band.

4. The method of claim 3, wherein adjusting the electrical stimulation to affect the brain signals in the gamma frequency band comprises adjusting the electrical stimulation to reduce the brain signals in the gamma frequency band.

5. The method of claim 1, the method further comprising: adjusting the electrical stimulation to affect the brain signals in another frequency band.

6. The method of claim 5, wherein adjusting the electrical stimulation to affect the brain signals in another frequency band comprises adjusting the electrical stimulation to increase the brain signals in another frequency band.

7. A method comprising:
 delivering electrical stimulation to a patient via one or more electrodes of a medical device, wherein the one or more electrodes are positioned proximate to a spinal cord of the patient and the electrical stimulation is formulated to alleviate pain in the patient;
 monitoring brain signals of a brain of the patient in two different frequency bands via an external brain activity monitoring device;
 determining a ratio of the brain signals in the two different frequency bands; and
 adjusting the electrical stimulation delivered via one or more electrodes to adjust the ratio in a manner that alleviates the pain.

8. A method comprising:
 delivering electrical stimulation to a patient via one or more electrodes of a medical device, wherein the one or more electrodes are positioned proximate to a spinal cord of the patient and the electrical stimulation is formulated to alleviate pain in the patient;
 monitoring brain signals of a brain of the patient in one or more frequency bands;
 adjusting the electrical stimulation to adjust the brain signals;
 determining a rate of change of the brain signals in response to the adjustments to the electrical stimulation; and
 further adjusting the electrical stimulation based on the determined rate of change.

9. The method of claim 1, wherein adjusting the electrical stimulation comprises adjusting an implantation location of the one or more electrodes based on the brain signals.

10. The method of claim 1, wherein adjusting the electrical stimulation comprises selecting different electrodes to be active on one or more implanted medical leads based on the brain signals.

11. The method of claim 1, wherein adjusting the electrical stimulation comprises adjusting one or more stimulation parameters selected from a group consisting of:
 pulse polarity;
 pulse voltage amplitude;
 pulse current amplitude;
 pulse rate;
 pulse pattern;
 waveform shape; and
 pulse width.

12. The method of claim 1, wherein the medical device comprises an external stimulator, the method further comprising:
 measuring the brain signals via a brain measuring device positioned on or attached to a head of a patient;
 monitoring the brain signals via the external brain activity monitoring device coupled to the brain measuring device; and
 adjusting the electrical stimulation delivered via the one or more electrodes based on the brain signals via the external stimulator, wherein the external stimulator is coupled to the brain measuring device during implantation of the one or more electrodes.

13. The method of claim 1, wherein the medical device comprises an implantable medical device (IMD), the method further comprising:
 measuring the brain signals via a brain measuring device positioned on or attached to a head of a patient;
 monitoring the brain signals via the external brain activity monitoring device coupled to the brain measuring device; and
 adjusting the electrical stimulation delivered by the IMD via the one or more electrodes based on the brain signals via a programmer coupled to the brain measuring device, wherein the programmer telemetrically communicates with the IMD.

14. The method of claim 1, wherein the medical device comprises an implantable medical device (IMD), the method further comprising:
 measuring and monitoring the brain signals via a brain measuring and monitoring device positioned on or attached to a head of a patient; and adjusting the electrical stimulation delivered by the IMD via the one or more implanted electrodes based on the brain signals via a programmer coupled to the brain measuring and monitoring device, wherein the programmer telemetrically communicates with the IMD.

15. The method of claim 1, further comprising:
adjusting drug delivery via an implanted drug pump based on the brain signals.

16. The method of claim 1, wherein the method is executed in an automated closed loop fashion in which the electrical stimulation is adjusted automatically based on the brain signals.

17. A method comprising:
delivering one or more drugs to a spinal cord of a patient via a drug pump of a medical device, wherein the drugs alleviate pain in the patient; monitoring brain signals in a gamma frequency band via an external brain activity monitoring device; and
adjusting the drug delivery based on the brain signals.

18. A system comprising:
an external brain activity monitoring device that monitors brain signals of a brain of a patient in a gamma frequency band;
one or more electrodes that deliver electrical stimulation to a patient, wherein the one or more electrodes are positioned proximate to the spinal cord of the patient and the electrical stimulation is formulated to alleviate pain in the patient; and
a stimulator device that generates the electrical stimulation delivered by the one or more electrodes, wherein the stimulator device adjusts the electrical stimulation based on the brain signals.

19. The system of claim 18, further comprising one or more implantable medical leads, wherein the one or more implanted electrodes are disposed on the one or more implanted medical leads and the electrical stimulation is delivered from the stimulator device to the one or more electrodes via the one or more implantable leads.

20. The system of claim 18, wherein:
the stimulator device adjusts the electrical stimulation to affect the brain signals in the gamma frequency band.

21. The system of claim 20, wherein the stimulator device adjusts the electrical stimulation to reduce the brain signals in the gamma frequency band.

22. The system of claim 18, wherein:
the stimulator device adjusts the electrical stimulation to affect the brain signals in another frequency band.

23. The system of claim 22, wherein the stimulator device adjusts the electrical stimulation to increase the brain signals in the another frequency band.

24. A system comprising:
an external brain activity monitoring device that monitors brain signals of a brain of a patient in two different frequency bands, and determines a ratio of the signals in the two different frequency bands;
one or more electrodes that delivery electrical stimulation to a patient, wherein the one or more electrodes are positioned proximate to the spinal cord of the patient and the electrical stimulation is formulated to alleviate pain in the patient; and
a stimulator device that generates the electrical stimulation delivered by the one or more electrodes and adjusts the electrical stimulation to adjust the ratio, wherein the stimulator device adjusts the electrical stimulation based on the brain signals.

25. The system of claim 18, further comprising:
a brain measuring device configured to be positioned on or attached to a head of the patient,
wherein the external brain activity monitoring device is coupled to the brain measuring device, and
wherein the stimulator device comprises an external stimulator coupled to the brain measuring device during implantation of the one or more implantable electrodes.

26. The system of claim 18, further comprising:
a brain measuring device configured to be positioned on or attached to a head of the patient; and
a programmer,
wherein the external brain activity monitoring device is coupled to the brain measuring device,
wherein the stimulator device comprises an implantable medical device, and
wherein the programmer is coupled to the external brain activity monitoring device and telemetrically communicates with the implantable medical device.

27. The system of claim 18, further comprising a programmer,
wherein the external brain activity monitoring device comprises a brain measuring and monitoring device positioned on or attached to a head of a patient,
wherein the stimulator device comprises an implantable medical device, and
wherein the programmer is coupled to the brain measuring and monitoring device and telemetrically communicates with the implantable medical device.

28. The system of claim 18, further comprising:
an implantable drug pump that adjusts drug delivery based on the brain signals.

29. The system of claim 18, wherein the system forms an automated closed loop system in which the stimulator device automatically adjusts the electrical stimulation based on the sensed brain signals.

30. A system comprising:
an external brain activity monitoring device that monitors brain signals of a brain of a patient in a gamma frequency band; and
an implantable drug pump that delivers drugs to a spinal cord of the patient, and adjusts drug delivery based on the brain signals, wherein the drugs alleviate pain in the patient.

31. The system of claim 30, wherein the system forms an automated closed loop system in which the implantable drug pump automatically adjusts drug delivery based on the brain signals.

32. A system comprising:
means for delivering electrical stimulation to a patient via one or more electrodes of a medical device, wherein the one or more electrodes are positioned proximate to a spinal cord of the patient and the electrical stimulation is formulated to alleviate pain in the patient;
means for monitoring brain signals of a brain of the patient in a gamma frequency band via an external brain activity monitoring device; and
means for adjusting the electrical stimulation delivered via the one or more electrodes based on the brain signals.

33. The system of claim 32, wherein the one or more electrodes are disposed on one or more implanted medical leads.

34. The system of claim 32, wherein:
the means for adjusting adjusts the electrical stimulation to affect the brain signals in the gamma frequency band.

35. The system of claim 34, wherein the means for adjusting the electrical stimulation to affect the brain signals in the gamma frequency band comprises means for adjusting the electrical stimulation to reduce the brain signals in the gamma frequency band.

36. The system of claim 32, wherein:
the means for adjusting adjusts the electrical stimulation to affect the brain signals in another frequency band.

37. The system of claim 36, wherein the means for adjusting adjusts the electrical stimulation to increase the brain signals in the another frequency band.

38. The system of claim 32, wherein:
the means for monitoring monitors the brain signals in two different frequency bands, and determines a ratio of the brain signals in the two different frequency bands; and
the means for adjusting adjusts the electrical stimulation to adjust the ratio in a manner that alleviates the pain.

39. The system of claim 32, wherein:
the means for adjusting adjusts the electrical stimulation to adjust the brain signals;
the means for monitoring determines a rate of change of the brain signals in response to the adjustments to the electrical stimulation; and
the means for adjusting further adjusts the electrical stimulation based on the determined rate of change.

40. The system of claim 32, wherein the means for adjusting the electrical stimulation comprises means for adjusting an implantation location of the one or more electrodes based on the brain signals.

41. The system of claim 32, wherein the means for adjusting the electrical stimulation comprises means for selecting different electrodes to be active on one or more implanted medical leads based on the brain signals.

42. The system of claim 32, wherein the means for adjusting the electrical stimulation adjusts one or more stimulation parameters selected from a group consisting of:
pulse polarity;
pulse voltage amplitude;
pulse current amplitude;
pulse rate;
pulse pattern;
waveform shape; and
pulse width.

43. The system of claim 32, wherein the means for delivering comprises an external stimulator, the system further comprising:
means for measuring the brain signals via a brain measuring device positioned on or attached to a head of a patient,
wherein the means for monitoring the brain signals is coupled to the brain measuring device, and
wherein the means for adjusting the electrical stimulation is coupled to the brain measuring device during implantation of the one or more electrodes.

44. The system of claim 32, wherein the means for delivering comprises an implantable medical device (IMD), the system further comprising:
means for measuring the brain signals via a brain measuring device positioned on or attached to a head of a patient;
wherein the means for monitoring the brain signals is coupled to the brain measuring device, and
wherein the means for adjusting the electrical stimulation comprises a programmer coupled to the brain measuring device, wherein the programmer telemetrically communicates with the IMD.

45. The method of claim 32, wherein the means for delivering comprises an implantable medical device (IMD), wherein:
the means for monitoring comprises means for measuring and monitoring the brain signals; and
wherein the means for adjusting comprises a programmer coupled to the means for measuring and monitoring, wherein the programmer telemetrically communicates with the IMD.

46. The system of claim 32, further comprising:
means for adjusting drug delivery via an implanted drug pump based on the brain signals.

47. The system of claim 32, wherein the system operates in an automated closed loop fashion in which the electrical stimulation is adjusted automatically based on the brain signals.

48. A system comprising:
means for delivering one or more drugs to a spinal cord of a patient via a drug pump of a medical device, wherein the drugs alleviate pain in the patient;
means for monitoring brain signals in a gamma frequency band via an external brain activity monitoring device; and
means for adjusting the drug delivery based on the brain signals.

49. A method comprising:
delivering electrical stimulation to a patient via one or more electrodes disposed on percutaneously implanted leads of an external medical device, wherein the one or more electrodes are positioned proximate to a spinal cord of a patient and the electrical stimulation is formulated to alleviate pain in the patient;
monitoring brain signals of a brain of the patient in a gamma frequency band via an external brain activity monitoring device;
adjusting the electrical stimulation delivered via the one or more electrodes based on the brain signals; and
determining whether to select the patient for treatment via an implantable medical device based on brain response to the therapy.

50. The method of claim 49, wherein adjusting the electrical stimulation comprises adjusting electrical stimulation delivered during a trial, and wherein determining whether to select the patient for treatment via an implantable medical device based on brain response to the therapy comprises determining whether to select the patient for treatment via an implantable stimulator device when the brain response demonstrates efficacy in pain reduction in the patient.

51. The method of claim 49, further comprising:
implanting the implantable medical device in the patient for spinal cord stimulation (SCS) when the brain response to the therapy demonstrates efficacy of the electrical stimulation in treating pain in the patient.

52. The method of claim 1, wherein the gamma frequency band is at least one of a low gamma frequency band from approximately 30 hertz (Hz) to approximately 60 Hz, a medium frequency gamma band from approximately 60 Hz to approximately 90 Hz, or a high frequency band from approximately 90 Hz to approximately 300 Hz.

53. The system of 18, wherein the gamma frequency band is at least one of a low gamma frequency band from approximately 30 hertz (Hz) to approximately 60 Hz, a medium frequency gamma band from approximately 60 Hz to approximately 90 Hz, or a high frequency band from approximately 90 Hz to approximately 300 Hz.

* * * * *

UNITED STATES PATENT AND TRADEMARK OFFICE
CERTIFICATE OF CORRECTION

| | | |
|---|---|---|
| PATENT NO. | : 8,185,207 B2 | Page 1 of 1 |
| APPLICATION NO. | : 13/167754 | |
| DATED | : May 22, 2012 | |
| INVENTOR(S) | : Molnar et al. | |

It is certified that error appears in the above-identified patent and that said Letters Patent is hereby corrected as shown below:

Col. 27, Line 58: "electrodes that delivery electrical" should read --electrodes that delivers electrical--

Col. 30, Line 59: "The system of 18" should read --The system of claim 18--

Signed and Sealed this
Second Day of October, 2012

David J. Kappos
*Director of the United States Patent and Trademark Office*